US012766485B2

(12) United States Patent
Choi et al.

(10) Patent No.: US 12,766,485 B2
(45) Date of Patent: Oct. 20, 2026

(54) IMMUNOGLOBULIN-BINDING PROTEIN VARIANTS WITH INCREASED ALKALI-TOLERANCE AND USE THEREOF

(71) Applicant: AMICOGEN, INC., Jinju-si (KR)

(72) Inventors: Su Lim Choi, Yongin-si (KR); So Young Park, Seongnam-si (KR); Sol A Park, Seongnam-si (KR); Yeo Won Sim, Suwon-si (KR)

(73) Assignee: AMICOGEN, INC., Jinju-si (KR)

( * ) Notice: Subject to any disclaimer, the term of this patent is extended or adjusted under 35 U.S.C. 154(b) by 647 days.

(21) Appl. No.: 18/305,522

(22) Filed: Apr. 24, 2023

(65) Prior Publication Data

US 2023/0356187 A1 Nov. 9, 2023

(30) Foreign Application Priority Data

May 3, 2022 (KR) ........................ 10-2022-0054786

(51) Int. Cl.

| | |
|---|---|
| ***C07K 14/00*** | (2006.01) |
| ***B01J 20/32*** | (2006.01) |
| ***C07K 1/22*** | (2006.01) |

(52) U.S. Cl.

CPC ............ *B01J 20/3274* (2013.01); *C07K 1/22* (2013.01)

(58) Field of Classification Search

CPC .... C07K 14/195; C07K 14/315; C07K 16/00; C07K 17/00; C07K 1/16; B01D 15/3809

See application file for complete search history.

(56) References Cited

U.S. PATENT DOCUMENTS

| | | | | |
|---|---|---|---|---|
| 2017/0327545 | A1* | 11/2017 | Rodrigo | C07K 14/195 |
| 2020/0190138 | A1 | 6/2020 | Chen et al. | |
| 2021/0162319 | A1 | 6/2021 | Hober | |

FOREIGN PATENT DOCUMENTS

| | | |
|---|---|---|
| JP | 2016-79149 | 5/2016 |
| JP | 2017-537632 | 12/2017 |
| JP | 2019-524088 | 9/2019 |
| KR | 10-2018-0005513 | 1/2018 |
| KR | 10-1857953 | 5/2018 |
| WO | 2005/033130 | 4/2005 |
| WO | 2016-096644 | 6/2016 |
| WO | 2016-121703 | 8/2016 |
| WO | 2021/109177 | 6/2021 |

OTHER PUBLICATIONS

KIPO, Written Decision on Registration of the corresponding Korean Patent Application No. 10-2022-0054786 dated Nov. 13, 2023.
Karlin, Samuel, et al. "Applications and statistics for multiple high-scoring segments in molecular sequences." Proceedings of the National Academy of Sciences 90.12 (Jun. 15, 1993): 5873-5877.
Pearson, William R. "[5] Rapid and sensitive sequence comparison with FASTP and FASTA." (1990): 63-98, Methods Enzymology., vol. 183 Academic Press, Inc.
JPO, Office Action of JP 2023-076167 dated May 28, 2024.
Stefan Kittler et al.," Protein L-More than just an affinity ligand ", Processes, 9(5), 874, May 17, 2021, total 14 pages.

* cited by examiner

*Primary Examiner* — Jeanette M Lieb
(74) *Attorney, Agent, or Firm* — LEX IP MEISTER, PLLC

(57) ABSTRACT

Provided are immunoglobulin-binding protein variants with increased alkali tolerance, and uses thereof, and more particularly to immunoglobulin-binding protein variants with increased alkali tolerance relative to the wild type due to mutations in amino acids at specific positions in the B3 domain of the immunoglobulin-binding proteins.

18 Claims, 4 Drawing Sheets

Specification includes a Sequence Listing.

IMMUNOGLOBULIN-BINDING PROTEIN VARIANTS WITH INCREASED ALKALI-TOLERANCE AND USE THEREOF

CROSS-REFERENCE TO RELATED APPLICATIONS

This application claims the benefit of Korean Patent Application No. 10-2022-0054786 filed on May 3, 2022 in the Korean Intellectual Property Office, the entire disclosure of which is hereby incorporated by reference.

REFERENCE TO AN ELECTRONIC SEQUENCE LISTING

The contents of the electronic sequence listing (LPP20230893US_SEQ.xml; Size: 69 K bytes; and Date of Creation: Apr. 24, 2023) is herein incorporated by reference in its entirety.

FIELD OF THE INVENTION

Provided are immunoglobulin-binding protein variants with increased alkali tolerance, and more particularly, immunoglobulin-binding protein variants in which an amino acid(s) at a specific position(s) in the B3 domain of the immunoglobulin-binding protein is mutated, resulting in increased alkali tolerance relative to the wild type, and uses thereof.

BACKGROUND OF THE INVENTION

When genetically engineered animal cells are cultured, monoclonal antibodies are secreted into the medium and are present at a very low concentration due to the mixture of proteins in the medium with other proteins secreted by the cells themselves. Therefore, removal of impurities other than the target monoclonal antibody is an important step in antibody production. Affinity chromatography using an antibody affinity ligand that can selectively recover only monoclonal antibodies from the medium is mainly used, and protein A, protein G, protein L, etc. may be used as antibody affinity ligands.

Immunoglobulin-binding bacterial proteins such as protein A, protein G, protein A/G, protein L, etc. are widely used to purify and detect immunoproteins (antibodies, antibody fragments, etc.). These immunoglobulin-binding proteins have different antibody binding modalities in terms of the recognition site on the antibody and the type of antibody they bind.

Among these, protein L was first isolated from the bacterium *Peptostreptococcus magnus* (*Finegoldia magna*) and, as its name indicates, was found to bind to immunoglobulins through a light chain interaction. Unlike protein A and protein G, which bind to the Fc site of immunoglobulins (antibodies), protein L binds to antibodies through a light chain (e.g., kappa) interaction. When compared to protein A and protein G, protein L has the advantage of being able to bind to a broader range of antibody types and can also bind to antibody fragments, such as single chain variable fragments (scFv) and Fab fragments due to the fact that it is not dependent on the heavy chain portion of the antibody.

Meanwhile, cleaning-in-place (CIP) is typically performed to remove various contaminants such as nucleic acids, lipids, proteins, and microorganisms that remain on a resin after antibody purification. The most widely used cleaning agent for resin is NaOH. However, such resins for protein-based purification are vulnerable to alkalis, and to make them more effective for antibody purification, it is necessary to develop immunoglobulin-binding proteins that are stable under alkaline conditions.

PRIOR ART

Patent Literature

Korean Patent No. 10-1857953

DETAILED DESCRIPTION OF THE INVENTION

Technical Problem

Provided herein are immunoglobulin-binding protein variants with increased alkali tolerance and uses thereof. The immunoglobulin-binding protein variant may be a variant of protein L or a functional portion thereof (e.g., the B3 domain), characterized by improved (increased) alkaline tolerance (e.g., immunoglobulin binding affinity, stability under alkaline conditions) compared to the wild-type protein or functional portion thereof.

More specifically, in one embodiment of the present disclosure, provided is a polypeptide in which at least one amino acid selected from the group consisting of the 28th amino acid (glutamic acid (Glu, E)), the 43rd amino acid (lysine (Lys, K)), the 13th amino acid (tyrosine (Tyr, Y)), the 51st amino acid (aspartic acid (Asp, D)), and the 60th amino acid (asparagine (Asn, N)), in the B3 domain of protein L (e.g., begins from a proline (Pro, P) which is the second amino acid in the amino acid sequence of SEQ ID NO: 4), is substituted with an amino acid different from the original.

In an example, the polypeptide may be a polypeptide comprising one or more substitutions in the B3 domain of protein L (e.g., begins from a proline (Pro, P) which is the second amino acid in the amino acid sequence of SEQ ID NO: 4), selected from the group consisting of the following:

- the 28th amino acid (E) is replaced with glycine (Gly, G), alanine (Ala, A), leucine (Leu, L), proline (Pro, P), or tryptophan (Trp, W);
- the 43rd amino acid (K) is replaced with proline (Pro, P) or glutamic acid (Glu, E);
- the 13th amino acid (Y) is replaced with phenylalanine (Phe, F);
- the 51st amino acid (D) is replaced with valine (Val, V) or threonine (Thr, T); and
- the 60th amino acid (N) is replaced with phenylalanine (Phe, F).

In another embodiment, a "polypeptide multimer" (hereinafter, "multimer") comprising two or more repeating units (monomers) each comprising, consisting essentially of, or consisting of the polypeptide is provided.

The polypeptide or the multimer thereof may further comprise one or more selected from the group consisting of the A, B1, B2, B4, C, W, and M domains of protein L.

Another embodiment provides a protein L variant comprising a polypeptide or a multimer comprising two or more repeats of the polypeptide as the B3 domain.

The polypeptide, the multimer thereof, and/or the protein L variant described above may have superior alkaline tolerance (e.g., immunoglobulin binding affinity, stability, etc. under alkaline conditions) compared to the wild-type protein L or a polypeptide comprising the B3 domain of the wild-type protein L (e.g., SEQ ID NO: 4).

Another embodiment provides a nucleic acid molecule encoding the polypeptide, the multimer thereof, and/or the protein L variant as described above.

Another embodiment provides a recombinant vector comprising the nucleic acid molecule, wherein the recombinant vector may be used as an expression vector for expressing the polypeptide, the multimer thereof, and/or the protein L variant in a suitable host cell.

Another embodiment provides a recombinant cell comprising the nucleic acid molecule or the recombinant vector. The recombinant cell may be a host cell transformed with the nucleic acid molecule or the recombinant vector, and may be a cell capable of expressing the polypeptide, the multimer thereof, and/or the protein L variant.

In another embodiment, a matrix (resin) is provided in which a plurality of ligands comprising the polypeptide, the multimer thereof comprising two or more repeating units of the polypeptide, or the protein L variant comprising the polypeptide or the multimer thereof as a B3 domain are coupled to a solid support. The matrix may be used for separating and/or purifying proteins by adsorption, e.g., chromatography.

In an embodiment, a composition for immunoglobulin binding, and/or a composition for immunoglobulin isolation and/or purification, comprising at least one selected from the group consisting of the following is provided:

(1) the polypeptide,
(2) a multimer comprising two or more repeating units of the polypeptide,
(3) a protein L variant comprising the polypeptide or the multimer thereof as a B3 domain,
(4) a nucleic acid molecule encoding the polypeptides, the multimer, or the protein L variant,
(5) a recombinant vector comprising the nucleic acid molecules,
(6) a recombinant cell comprising the nucleic acid molecule or the recombinant vector; and
(7) a matrix comprising a plurality of ligands comprising the polypeptide, the multimer thereof, or the protein L variant coupled to a solid support.

Another embodiment provides use for immunoglobulin binding, and/or immunoglobulin isolation and/or purification, comprising at least one selected from the group consisting of the following is provided:

(1) the polypeptide,
(2) a multimer comprising two or more repeating units of the polypeptide,
(3) a protein L variant comprising the polypeptide or the multimer thereof as a B3 domain,
(4) a nucleic acid molecule encoding the polypeptides, the multimer, or the protein L variant,
(5) a recombinant vector comprising the nucleic acid molecules,
(6) a recombinant cell comprising the nucleic acid molecule or the recombinant vector; and
(7) a matrix comprising a plurality of ligands comprising the polypeptide, the multimer thereof, or the protein L variant coupled to a solid support.

Another embodiment provides a composition for the isolation and/or purification of immunoglobulins comprising at least one selected from the group consisting of the following is provided:

(a) the polypeptide,
(b) the multimer comprising two or more repeating units of the polypeptide,
(c) a protein L variant comprising the polypeptide or the multimer thereof as a B3 domain; and
(d) a matrix for chromatography, wherein a plurality of ligands comprising the polypeptide, the multimer thereof, or the protein L variant are coupled to a solid support.

Another embodiment provides use for the isolation and/or purification of immunoglobulins comprising at least one selected from the group consisting of the following is provided:

(a) the polypeptide,
(b) the multimer comprising two or more repeating units of the polypeptide,
(c) a protein L variant comprising the polypeptide or the multimer thereof as a B3 domain; and
(d) a matrix for chromatography, wherein a plurality of ligands comprising the polypeptide, the multimer thereof, or the protein L variant are coupled to a solid support.

In another embodiment, provided is a method of isolating and/or purifying an immunoglobulin, comprising the step of adsorbing immunoglobulin by contacting a sample containing the immunoglobulin (e.g. a liquid sample) with at least one selected from the group consisting of the following:

(a) the polypeptide,
(b) the multimer comprising two or more repeating units of the polypeptide,
(c) a protein L variant comprising the polypeptide or the multimer thereof as a B3 domain; and
(d) a matrix for chromatography, wherein a plurality of ligands comprising the polypeptides, the multimer, or the protein L variant are coupled to a solid support.

In another embodiment, there is provided a method of isolating or purifying one or more target compounds from a liquid comprising the step of adsorbing the target compound by contacting a sample containing the target compound (e.g. a liquid sample) with at least one selected from the group consisting of the following:

(a) the polypeptide,
(B) the multimer comprising two or more repeating units of the polypeptide,
(c) a protein L variant comprising the polypeptide or the multimer thereof as a B3 domain; and
(d) a matrix for chromatography, wherein a plurality of ligands comprising the polypeptides, the multimer, or the protein L variant are coupled to a solid support.

Technical Solution

Provided herein is a protein L B3 domain variant with enhanced alkali tolerance and uses thereof.

Definition of Terms

In this specification, when a polynucleotide (which may be used interchangeably with a "gene or nucleic acid molecule") or polypeptide (which may be used interchangeably with a "protein") "comprises a particular nucleic acid sequence or amino acid sequence" or "consists (essentially) of a particular nucleic acid sequence or amino acid sequence" or "is represented by a particular nucleic acid sequence or amino acid sequence," this may mean that the polynucleotide or polypeptide essentially comprises the particular nucleic acid sequence or amino acid sequence, or may be construed to include a "substantially equivalent sequence" in which a modification (deletion, substitution (replacement), modification, and/or addition) has been made to the specific nucleic acid sequence or amino acid sequence to the extent that the polynucleotide or polypeptide retains its original function (binding to the light chain of an immunoglobulin) and/or its intended function (e.g., increased alkali tolerance relative to the wild-type protein L B3 domain).

In one example, a reference to a polynucleotide or polypeptide "comprising a particular nucleic acid sequence or amino acid sequence" or "consisting (essentially) of or represented by a particular nucleic acid sequence or amino acid sequence" may mean that the polynucleotide or polypeptide, (i) comprises, essentially consists of, or consists of the particular nucleic acid sequence or amino acid sequence; or (ii) comprises, essentially consists of, or consists of a nucleic acid sequence or amino acid sequence having a sequence identity of 80% or more, 85% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more with the particular nucleic acid sequence or amino acid sequence, and retaining the original function and/or intended function. In the present disclosure, the original function may be the ability to bind immunoglobulins (particularly, the light chain region) of the wild-type protein L B3 domain (in the case of an amino acid sequence), or the ability to encode a protein having such immunoglobulin binding affinity (in the case of a nucleic acid sequence), and the intended function may be the ability to have increased alkali tolerance (in the case of an amino acid sequence) or the ability to encode a protein having such increased alkali tolerance (in the case of a nucleic acid sequence) relative to the wild-type protein L B3 domain.

The polypeptides provided herein may comprise an amino acid sequence defined by a particular sequence number or may be a functional variant thereof. The "functional variants" include all similar sequences comprising one or more additional variations at amino acid positions that do not affect the enhanced chemical stability and/or affinity (binding capacity) of the polypeptide for immunoglobulins in an environment of increased pH values.

As used herein, the term "sequence identity" refers to the degree of identity with a given nucleic acid sequence or amino acid sequence, which may be expressed as a percentage (%). For nucleic acid sequences, homology can be determined, for example, using the algorithm BLAST (Karlin and Altschul, Pro. Natl. Acad. Sci. USA, 90, 5873, 1993) or FASTA (Pearson, Methods Enzymol., 183, 63, 1990). Based on the algorithm BLAST, programs called BLASTN or BLASTX have been developed (http://www.ncbi.nlm.nih.gov).

As used herein, "an amino acid residue at a particular position in the amino acid sequence of a polypeptide" can be interpreted to include an amino acid residue at a particular position in the amino acid sequence or an amino acid residue at a position corresponding to the particular position in an isotype protein of homologous origin and/or a heterologous protein having the same activity as the protein.

In the amino acid sequences of the polypeptides provided herein, wherein the first N-terminal residue is methionine (M), the methionine may be present in nature or may be produced by recombinant technology. If the polypeptides provided herein are produced by recombination, polypeptides comprising an amino acid sequence other than methionine (M) as the first N-terminal residue and/or a signal peptide located at the N-terminus are also included in the scope of the present disclosure. Furthermore, if the N-terminal first residue of the amino acid sequence of a protein is not methionine, methionine may be added to the N-terminus of the first residue if the protein is produced recombinantly.

As used herein, amino acid position starts from the second amino acid following the methionine in the case of a recombinant protein comprising methionine (M) as the first amino acid residue of the N-terminus, unless otherwise noted. For example, in the polypeptide of SEQ ID NO: 4 comprising methionine (M) as the first amino acid of the N-terminus, the term "28th amino acid" refers to the amino acid residue positioned 28th (i.e., corresponding to the 29th amino acid in SEQ ID NO: 4) after the first amino acid, methionine, with proline (P) as the second amino acid.

As used herein, one (1) to three (3) letters of an amino acid refer to the following amino acids in accordance with standard abbreviations in the biochemical field:

A (Ala): Alanine; C (Cys): Cysteine; D (Asp): Aspartic acid; E (Glu): Glutamic acid; F (Phe): Phenylalanine; G (Gly): Glycine; H (His): Histidine; I (Ile): Isoleucine; K (Lys): Lysine; L (Leu): Leucine; M (Met): Methionine; N (Asn): Asparagine; O (Ply): Pyrrolysine; P (Pro): Proline; Q (Gln): Glutamine; R (Arg): Arginine; S(Ser): Serine; T (Thr): Threonine; U (Sec): Selenocysteine; V (Val): Valine; W (Trp): Tryptophan; Y (Tyr): Tyrosine.

As used herein, "(1 letter amino acid)(amino acid position)(1 letter amino acid)" means that the leading amino acid is replaced with the trailing amino acid at the corresponding amino acid position in the native polypeptide. For example, E28G means that the glutamic acid (E) at residue 28 of the native polypeptide is replaced by a glycine (G). In addition, a slash (/) mark on a trailing amino acid can mean "or". For example, E28G/A can mean that the glutamic acid (E) at residue 28 of the native polypeptide is substituted with either glycine (G) or alanine (A).

As used herein, the term "about" is intended to include any number in the same or similar range as the number that follows, and may be construed to include, but is not limited to, a range of ±0.5, ±0.4, ±0.3, ±0.2, ±0.1, ±0.05, or ±0.01, relative to the number that follows.

Hereinafter, the present disclosure will be described in more detail.

Immunoglobulin-Binding Protein Variants: Protein L B3 Domain Variants, Multimers Comprising the Same, Immunoglobulin-Binding Proteins, and Protein L Variants.

Provided herein are immunoglobulin-binding protein variants with increased alkali tolerance and uses thereof. The immunoglobulin-binding protein variants may be variants of protein L or a functional portion thereof (e.g., the B3 domain), characterized by improved (increased) alkaline tolerance (e.g., immunoglobulin binding affinity, stability under alkaline conditions) relative to the wild-type protein or functional portion thereof.

The immunoglobulin-binding protein of the present disclosure was first isolated from *Peptostreptococcus magnus* (*Finegoldia magna*), and was found to bind to immunoglobulin via a light chain interaction, and thus, was named protein L. Protein L from *Peptostreptococcus magnus* (e.g., NCBI Accession No. AAA25612.1) consists of 719 amino acid residues and has a molecular mass of 95 kD (as measured by SDS-PAGE in the presence of reducing agent (2-mercaptoethanol)) or 76 kD (as measured by gelchromatography in the presence 6 M guanidine HCl). Unlike protein A and protein G, which bind to the Fc site of immunoglobulins (antibodies), protein L binds to antibodies through light chain (e.g., kappa) interactions. Because protein L is not affected by the heavy chain portion of the antibody, it can bind to a wider range of antibody types compared to protein A and protein G. It can bind to all subtypes of antibodies, including IgG, IgM, IgA, IgE, IgD, etc. and can also bind to antibody fragments such as single chain variable fragments (scFv), Fab fragments, etc.

This immunoglobulin light chain (kappa) binding activity makes protein L advantageous for the purification of antibodies (full-length or fragment) containing kappa type light chains (in whole or in part).

Accordingly, the immunoglobulin-binding protein variants of the present disclosure may be modified based on protein L, particularly the B3 domain of protein L. The protein L may be from *Peptostreptococcus magnus*, e.g., represented by the amino acid sequence of NCBI Accession No. AAA25612.1 (SEQ ID NO: 50), or may have a sequence identity of 80% or more, 85% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more with the amino acid sequence while retaining the ability to bind immunoglobulin (specifically, the light chain region), but is not limited thereto.

The B3 domain of protein L may be the B3 domain of protein L from *Peptostreptococcus magnus* (e.g., SEQ ID NO: 50), and may be represented by the amino acid sequence of SEQ ID NO: 4, or having a sequence identity of 80% or more, 85% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more with SEQ ID NO: 4 while retaining immunoglobulin (specifically, light chain region) binding affinity, but is not limited thereto. The B3 domain of protein L may be, but is not limited to, that encoded by the nucleic acid sequence of SEQ ID NO: 3.

By introducing a modification by amino acid substitution at a predetermined position of the B3 domain, the alkaline tolerance of the B3 domain or a polypeptide, and/or a protein L variant comprising the same can be increased while maintaining the binding affinity to immunoglobulins (particularly the light chain region thereof).

In one embodiment, a polypeptide (B3 domain variant of protein L) is provided wherein, in the B3 domain of protein L, one or more amino acids selected from the group consisting of glutamic acid (Glu, E) corresponding to the 28th amino acid residue, lysine (Lys, K) corresponding to the 43rd amino acid residue, tyrosine (Tyr, Y) corresponding to the 13th amino acid residue, aspartic acid (Asp, D) corresponding to the 51st amino acid residue, and asparagine (Asn, N) corresponding to the 60th amino acid residue, wherein one or more (e.g., one, two, three, four, or five) amino acids selected from the group consisting of Lys, K, Tyr, Y, and Asn, N are substituted with amino acids different from the original.

The amino acids different from the original may be one selected from the group consisting alanine (A, Ala), asparagine (N, Asn), threonine (T, Thr), glutamic acid (E, Glu), serine (S, Ser), valine (V, Val), isoleucine (I, Ile), leucine (L, Leu), aspartic acid (D, Asp), cysteine (C, Cys), glutamine (Q, Gln), methionine (M, Met), phenylalanine (F, Phe), proline (P, Pro), tryptophan (W, Trp), tyrosine (Y, Tyr), arginine (R, Arg), histidine (H, His), lysine (K, Lys), and glycine (G, Gly), and may be amino acid different from the amino acid residues at the corresponding positions in the B3 domain of the wild-type protein L.

In one embodiment, the polypeptide may comprise one or more substitutions (e.g., one, two, three, four, or five) selected from the following in the B3 domain of protein L:

- the 28th amino acid (E) is replaced by glycine (Gly, G), alanine (Ala, A), leucine (Leu, L), proline (Pro, P), or tryptophan (Trp, W);
- the 43rd amino acid (K) is replaced by proline (Pro, P) or glutamic acid (Glu, E);
- the 13th amino acid (Y) is replaced by phenylalanine (Phe, F);
- the 51st amino acid (D) is replaced by valine (Val, V) or threonine (Thr, T); and
- the 60th amino acid (N) is replaced by phenylalanine (Phe, F).

In another embodiment, the polypeptide may be a polypeptide in which the 28th amino acid (E) in the B3 domain of protein L is substituted with glycine (Gly, G), alanine (Ala, A), leucine (Leu, L), proline (Pro, P), or tryptophan (Trp, W), for example, glycine (Gly, G).

In another embodiment, in the B3 domain of protein L, the 28th amino acid (E) of the polypeptide may be substituted with glycine (Gly, G), alanine (Ala, A), leucine (Leu, L), proline (Pro, P), or tryptophan (Trp, W). The polypeptide variant may further comprise one or more substitutions selected from the following:

- starting from the second amino acid, proline (Pro, P), in the amino acid sequence of SEQ ID NO: 4,
- the 43rd amino acid (K) is replaced by proline (Pro, P) or glutamic acid (Glu, E);
- the 13th amino acid (Y) is replaced by phenylalanine (Phe, F);
- the 51st amino acid (D) is replaced by valine (Val, V) or threonine (Thr, T); and
- the 60th amino acid (N) is replaced by phenylalanine (Phe, F).

For example, the polypeptide may comprise the following amino acid variations in the B3 domain of protein L:

E28G (wherein the 28th amino acid, glutamic acid (E) is replaced by glycine (G); single amino acid substitutions herein are shown and interpreted in the same manner), E28A, E28L, E28P, E28W, E28G+Y13F, E28G+K43P (wherein the 28th amino acid, glutamic acid (E), is replaced by glycine (G) and the 43rd amino acid, lysine (K), is replaced by proline (P), multiple amino acid substitutions herein are shown and interpreted in the same manner), E28G+D51V, E28G+N60E, E28L, E28P, E28W, E28G+K43E, E28G+D51T, E28G+N60F, or Y13F+E28G+K43P.

The B3 domain of protein L (wild type) may comprise the amino acid sequence of SEQ ID NO: 4.

The amino acid positions of the B3 domain of protein L described herein start from the second amino acid, proline (Pro, P), in the amino acid sequence of SEQ ID NO: 4. That is, the 28th amino acid (E) (E28) described herein corresponds to the 29th amino acid of SEQ ID NO: 4, and the 43rd amino acid (K) (K43) corresponds to the 44th amino acid of SEQ ID NO: 4, the 13th amino acid (Y) (Y13) corresponds to the 14th amino acid of SEQ ID NO: 4, the 51st amino acid (D) (D51) corresponds to the 52nd amino acid of SEQ ID NO: 4, and the 60th amino acid (N) (N60) corresponds to the 61st amino acid of SEQ ID NO: 4.

In one embodiment, the polypeptide (protein L B3 domain variant), based on the amino acid sequence of SEQ ID NO: 4, comprises

- an amino acid sequence that is modified by the introduction of the E28A mutation (SEQ ID NO: 7);
- an amino acid sequence that is modified by the introduction of the E28G mutation (SEQ ID NO: 8);

an amino acid sequence that is modified by the introduction of the E28G+Y13F mutation (SEQ ID NO: 9);

an amino acid sequence that is modified by the introduction of the E28G+K43P mutation (SEQ ID NO: 10);

an amino acid sequence that is modified by the introduction of the E28G+D51V mutation (SEQ ID NO: 11);

an amino acid sequence that is modified by the introduction of the E28G+N60E mutation (SEQ ID NO: 12).

an amino acid sequence that is modified by the introduction of the E28L mutation (SEQ ID NO: 23);

an amino acid sequence that is modified by the introduction of the E28P mutation (SEQ ID NO: 24);

an amino acid sequence that is modified by the introduction of the E28W mutation (SEQ ID NO: 25);

an amino acid sequence that is modified by the introduction of the E28G+K43E mutation (SEQ ID NO: 26);

an amino acid sequence that is modified by the introduction of the E28G+D51T mutation (SEQ ID NO: 27);

an amino acid sequence that is modified by the introduction of the E28G+N60F variant (SEQ ID NO: 28); or an amino acid sequence that is modified by the introduction of the Y13F+E28G+K43P mutation (SEQ ID NO: 47).

The amino acid sequence of the above polypeptide (protein L B3 domain variant) is summarized in Table 1 below:

Another embodiment provides a multimer comprising two or more of the polypeptides as repeating units (monomers). In one embodiment, the multimers may comprise two or more repeating units comprising (or consisting of) the aforementioned polypeptides, such as two, three, four, five, six, seven, eight, nine, or ten repeating units. For example, the multimer may be one represented by SEQ ID NO: 49 (including four consecutive sequences of SEQ ID NO: 47), but are not limited thereto.

Another embodiment provides an immunoglobulin-binding protein comprising the polypeptide or the multimer thereof.

In one embodiment, the immunoglobulin-binding protein may further comprise, in addition to the polypeptide or the multimer, one or more selected from the group consisting of the A, B1, B2, B4, C, W, and M domains of protein L.

Other embodiment provides a protein L variant comprising the polypeptide or the multimer.

The polypeptides (protein L B3 domain variants), multimers thereof, immunoglobulin-binding proteins, and/or protein L variants provided herein may have increased alkali tolerance compared to the wild-type B3 domain (SEQ ID NO: 4) or the multimer, immunoglobulin-binding protein, and/or protein L comprising thereof. For example, the binding affinity of the polypeptides, multimers, immunoglobu-

TABLE 1

| SEQ ID NO: | Description | Sequence |
|---|---|---|
| 4 | Wild-type Protein L B3 domain | MPKEEVTIKANLIYADGKTQTAEFKGTFEEATAEAYR YADLLAKENGKYTVDVADKGYTLNIKFAGKEKTPEE |
| 7 | Protein L B3 domain variant (E28A) | MPKEEVTIKANLIYADGKTQTAEFKGTF**A**EATAEAYR YADLLAKENGKYTVDVADKGYTLNIKFAGKEKTPEE |
| 8 | Protein L B3 domain variant (E28G) | MPKEEVTIKANLIYADGKTQTAEFKGTF**G**EATAEAYR YADLLAKENGKYTVDVADKGYTLNIKFAGKEKTPEE |
| 9 | Protein L B3 domain variant (E28G/Y13F) | MPKEEVTIKANLI**F**ADGKTQTAEFKGTF**G**EATAEAYR YADLLAKENGKYTVDVADKGYTLNIKFAGKEKTPEE |
| 10 | Protein L B3 domain variant (E28G/K43P) | MPKEEVTIKANLIYADGKTQTAEFKGTF**G**EATAEAYR YADLLA**P**ENGKYTVDVADKGYTLNIKFAGKEKTPEE |
| 11 | Protein L B3 domain variant (E28G/D51V) | MPKEEVTIKANLIYADGKTQTAEFKGTF**G**EATAEAYR YADLLAKENGKYTV**V**VADKGYTLNIKFAGKEKTPEE |
| 12 | Protein L B3 domain variant (E28G/N60E) | MPKEEVTIKANLIYADGKTQTAEFKGTF**G**EATAEAYR YADLLAKENGKYTVDVADKGYTL**E**IKFAGKEKTPEE |
| 23 | Protein L B3 domain variant (E28L) | MPKEEVTIKANLIYADGKTQTAEFKGTF**L**EATAEAYR YADLLAKENGKYTVDVADKGYTLNIKFAGKEKTPEE |
| 24 | Protein L B3 domain variant (E28P) | MPKEEVTIKANLIYADGKTQTAEFKGTF**P**EATAEAYR YADLLAKENGKYTVDVADKGYTLNIKFAGKEKTPEE |
| 25 | Protein L B3 domain variant (E28W) | MPKEEVTIKANLIYADGKTQTAEFKGTF**W**EATAEAYR YADLLAKENGKYTVDVADKGYTLNIKFAGKEKTPEE |
| 26 | Protein L B3 domain variant (E28G/K43E) | MPKEEVTIKANLIYADGKTQTAEFKGTF**G**EATAEAYR YADLLA**E**ENGKYTVDVADKGYTLNIKFAGKEKTPEE |
| 27 | Protein L B3 domain variant (E28G/D51T) | MPKEEVTIKANLIYADGKTQTAEFKGTF**G**EATAEAYR YADLLAKENGKYTV**T**VADKGYTLNIKFAGKEKTPEE |
| 28 | Protein L B3 domain variant (E28G/N60F) | MPKEEVTIKANLIYADGKTQTAEFKGTF**G**EATAEAYR YADLLAKENGKYTVDVADKGYTL**F**IKFAGKEKTPEE |
| 47 | Protein L B3 domain variant (Y13F/E28G/K43P) | MPKEEVTIKANLI**F**ADGKTQTAEFKGTF**G**EATAEAYR YADLLA**P**ENGKYTVDVADKGYTLNIKFAGKEKTPEE |

(In Table 1, mutated amino acids are shown in bold and underlined)

lin-binding proteins, and/or protein L variants provided herein to bind an immunoglobulin (e.g., an IgG (IgG1, IgG2, IgG,3, or IgG4)) or a fragment comprising a light chain region thereof (e.g., scFv, Fab, or the like) may be increased under basic conditions (e.g., pH 9 or greater, pH 9.5 or greater, pH 10 or greater, pH 10.5 or greater, pH 11 or greater, pH 11.5 or greater, pH 12 or greater, pH 12.5 or greater, or pH 13 or greater (The upper limit may be pH 14)) by about 5% or more, about 10% or more, about 15% or more, about 20% or more, about 25% or more, or about 30% or more, compared to the wild-type B3 domain (SEQ ID NO: 4) or a polypeptide or a multimer comprising thereof, an immunoglobulin-binding protein, and/or protein L, but is not limited thereto. In particular, the multimers may have an increased ability to bind immunoglobulin or fragments thereof under basic conditions, compared to the wild-type B3 domain, of about 1.5-fold or more, about 1.7-fold or more, about 2-fold or more, about 2.3-fold or more, about 2.5-fold or more, or about 2.7-fold or more, but are not limited thereto.

As used herein, the immunoglobulin may be derived from a human, a primate such as a monkey, a rodent such as a mouse, a rat, or the like, and may be selected from various subtypes of IgG (IgG1, IgG2, IgG3, or IgG4), IgA, IgD, IgE, IgM, and the like. The polypeptides (protein L B3 domain variants) and/or the multimers, immunoglobulin-binding proteins, and/or protein L variants comprising thereof provided herein may bind to the light chain region of an immunoglobulin. Accordingly, the immunoglobulins to which the polypeptides (protein L B3 domain variants), multimers, immunoglobulin-binding proteins, and/or protein L variants provided herein are capable of binding may be in their complete form or in fragmented form including the light chain, such as, but not limited to, scFv, Fab, $(scFv)_2$, Fab, Fab', or $F(ab')_2$.

In one embodiment, the polypeptides, multimers, immunoglobulin-binding proteins, and/or protein L variants provided herein may be non-naturally occurring, e.g., produced by recombinant methods or chemical synthesis, but are not limited thereto.

Nucleic Acid Molecules, Recombinant Expression Vectors, Recombinant Cells

Other embodiment provides a nucleic acid molecule encoding the above described polypeptide (B3 domain variant), multimer, immunoglobulin-binding protein, or protein L variant.

Another embodiment provides a recombinant vector comprising the nucleic acid molecule. The recombinant vector may be an expression vector capable of expressing the nucleic acid molecule as a protein in a suitable host cell. The recombinant vector may be used as an expression vector for expressing the polypeptide, multimer, and/or protein L variant in an appropriate host cell.

Another embodiment provides a recombinant cell comprising the nucleic acid molecule or recombinant vector. The recombinant cell may be a suitable host cell into which the nucleic acid molecule or recombinant vector is introduced (transformed).

Additionally, the polypeptide, the multimer thereof, immunoglobulin-binding proteins, or protein L variants may be used in an immobilized rather than in a free state. The immobilization can be prepared by conventional methods known in the art, and as a carrier for immobilization, natural polymers such as fibrin, starch, dextran, agarose, and the like; synthetic polymers such as polyacrylamide, polyacrylate, polymethacylate, and Eupergit C; or silica, bentonite, and minerals such as metals may be used. It is also possible to conjugate the polypeptide, multimer, immunoglobulin-binding protein, or protein L variant to the carrier by covalent, ionic, or hydrophobic bondings, physical adsorption, microencapsulation, or the like. It is also possible to immobilize the polypeptide, multimer, immunoglobulin-binding protein, or protein L variant by forming a covalent bond between the carrier-enzyme conjugate and the polypeptide, multimer, immunoglobulin-binding protein, or protein L variant by the action of glutaraldehyde, cyanogen bromide, or the like. It is also possible to immobilize and use microbial cells comprising the polypeptide, multimer, immunoglobulin-binding protein, or protein L variants without the need to purify the polypeptides, the multimer thereof, immunoglobulin-binding proteins, or protein L variants. In such whole cell immobilization, techniques such as cell entrapment or surface display can be applied to increase the reactivity of the polypeptide, multimer, immunoglobulin-binding protein, or protein L variant in the microorganism.

The nucleic acid sequences described herein may be subject to various modifications in the coding region without altering the amino acid sequence and/or function of the protein expressed from the coding region, taking into account codons that are preferred in microorganisms that wish to express the polypeptide, multimer, immunoglobulin-binding protein, or protein L variant due to degeneracy of codons.

The introduction of the nucleic acid molecule or vector may be performed by any known transfection method suitable to those skilled in the art. As used herein, the term "transfection" refers to the introduction of a vector comprising a nucleic acid molecule encoding a target protein (foreign protein) into a host cell such that the protein encoded by the nucleic acid molecule can be expressed in the host cell. The transfected nucleic acid molecule may be inserted within a chromosome of the host cell and/or located outside the chromosome, as long as it can be expressed in the host cell. Further, the nucleic acid molecule comprises DNA and/or RNA encoding a target protein (the polypeptide, multimer, immunoglobulin-binding protein, or protein L variant). The nucleic acid molecule can be introduced into and expressed in a host cell, and the form in which it is introduced is not limited. For example, the nucleic acid molecule may be introduced into the host cell in the form of an expression cassette, which is a genetic construct containing all the elements necessary to express itself. The expression cassette may include expression regulatory elements such as a promoter, a transcription termination signal, a ribosome binding site, and/or a translation termination signal, which are typically operably linked to the nucleic acid molecule. The expression cassette may be in the form of an expression vector capable of self-replication. Alternatively, the nucleic acid molecule may be introduced into the genome of a host cell in its native form and operably linked to a sequence required for expression in the host cell. As used above, the term "operably linked" may mean that the nucleic acid molecule is functionally linked to an expression regulatory element (e.g., a promoter) such that the expression regulatory element can perform transcriptional regulation (e.g., transcription initiation) of the nucleic acid molecule encoding the target protein (foreign protein). Functional linkage can be accomplished using genetic recombination techniques known in the art, such as, but not limited to, by conventional site-specific DNA cleavage and ligation.

The method of transfecting the nucleic acid molecule into a host cell can be performed by any method of introducing the nucleic acid into a cell (microorganism), and can be performed by appropriately selecting a transformation technique known in the art depending on the host cell. Known transfection methods include electroporation, calcium phosphate ($CaPO_4$) precipitation, calcium chloride ($CaCl_2$) precipitation, microinjection, polyethylene glycol (PEG) precipitation, polyethylene glycol-mediated uptake, DEAE-dextran, and cationic liposomes, lipofection, lithium acetate-DMSO method, heat shock method, particle gun bombardment, silicon carbide whiskers, sonication, and the like, but are not limited to.

The introduction (insertion) of a nucleic acid molecule into the host cell genome (chromosome) may be performed by any method known in the art, including, for example, an RNA-guided endonuclease system (RNA-guided endonuclease system or CRISPR system; e.g., (a) an RNA-guided endonuclease (e.g., a Cas9 protein, etc.), a gene encoding the gene, or a vector comprising the gene; and (b) a guide RNA (e.g., single guide RNA (sgRNA), etc.), a DNA encoding the same, or a vector comprising the DNA; a mixture (e.g., a mixture of an RNA-guide endonuclease protein and a guide RNA, etc.); a complex (e.g., a ribonucleic acid fusion protein (RNP)), one or more selected from the group consisting of, but not limited to, recombinant vectors (e.g., co-containing vectors comprising an RNA-guide endonuclease-encoding gene and guide RNA-encoding DNA), and the like.

As used herein, the term "vector" refers to a DNA construct comprising a sequence of a nucleic acid molecule encoding a target protein operably linked to a suitable regulatory sequence for expression of the target protein in a suitable host. The regulatory sequence may comprise a promoter capable of initiating transcription, any operator sequence for regulating transcription, a sequence encoding a suitable mRNA ribosome binding site, and/or a sequence regulating termination of transcription and/or decoding. After transformation into a suitable host cell, the vector may be expressed independently of the genome of the host cell, or may be integrated into the genome of the host cell.

The vectors used herein are not specifically limited to those that are capable of replication in a host cell, and may be selected from any one of vectors in use in the art. Examples of commonly used vectors include plasmids, cosmids, viruses, bacteriophages, and the like, either in their natural or recombinant state. For example, as a phage vector or cosmid vector, pWE15, M13, MBL3, MBL4, IXII, ASHII, APII, t10, t11, Charon4A, and Charon21A can be used. As plasmid vectors, pBC (e.g., pBC-KS(+)), pBR (e.g., pBR322, pBR325), pUC (e.g., pUC118 and pUC119), pBluescriptII, pGEM, pTZ, pCL, and pET (e.g., pET-22b (+)), *Bacillus subtilis*-derived plasmids (e.g., pUB110, pTP5), animal virus-derived plasmids, such as retroviruses, adenoviruses, or vaccinia viruses, and insect virus-derived plasmids, such as baculoviruses, can be used, but are not limited thereto.

The host cell may be selected from the group consisting of any conventionally used unicellular organism, e.g., prokaryotic microorganisms such as various bacteria (e.g., genus *Escherichia*, genus *Clostridia*, etc.) and eukaryotic microorganisms such as yeast, e.g., microorganisms of the genus *Clostridia* (e.g., *Clostridium acetobutylicum, Clostridium beijerinckii, Clostridium saccharoperbutylacetonicum*, or *Clostridium saccharobutylicum*), microorganisms of the genus *Escherichia* (e.g., *Escherichia coli*), and the like, but not limited thereto.

The vectors used herein may be known expression vectors and/or vectors for the insertion of a nucleic acid molecule into a host cell chromosome. The insertion of the nucleic acid molecule into the host cell chromosome may be accomplished by any method known in the art, such as, but not limited to, homologous recombination or CRISPR systems. The vector may further comprise a selection marker to confirm the insertion into the chromosome. The selection marker may be selected from genes conferring selectable phenotypes, such as drug resistance, nutritional requirements, resistance to cytotoxic agents, or expression of surface proteins, in order to select cells transformed with the vector, i.e. to confirm the insertion of the polynucleotide. In an environment treated with a selective agent, only cells expressing the selective marker will survive or exhibit a different phenotype, allowing for selection of the transformed cells.

Another embodiment provides a method of preparing the polypeptide (a B3 domain variant), the multimer thereof, immunoglobulin-binding protein, or protein L variant as described above, comprising the step of expressing the nucleic acid molecule in a suitable host cell. The method of preparation may comprise the step of culturing the recombinant cells described above, and may further comprise the step of isolating and/or purifying the polypeptide, the multimer thereof, immunoglobulin-binding protein, or protein L variant from the culture.

Matrix Containing B3 Domain Variants (Resin)

Another embodiment provides a matrix (resin) in which the polypeptide (B3 domain variant), the multimer thereof, immunoglobulin-binding protein, or protein L variant is coupled to a solid support. The matrix may be a chromatographic matrix for use in techniques for separating and/or purifying proteins by adsorption, such as, but not limited to, (affinity) chromatography.

In the matrix, the polypeptide, the multimer thereof, immunoglobulin-binding protein, or protein L variant is used as a ligand to be bound (coupled) to a solid support, and may be used in two or more plurals. In one embodiment, the matrix for chromatography may be a plurality of multimers coupled to a solid support, but is not limited thereto.

The solid support may be suitably selected from any suitable known class of solid supports capable of coupling polypeptides, such as those used in conventional affinity separation matrices. For example, the solid support may be an organic or inorganic material.

In one example, the solid support may be an organic material, and may be based on a polymer exposing a hydrophilic surface to an aqueous medium and/or exposing hydroxy (—OH), carboxy (—COOH), carboxamido (—CONH2, possibly in N-replaced withm), amino (—NH2, possibly in replaced withm), oligo- or polyethylenoxy groups. The polymer may be based on a polysaccharide such as dextran, starch, cellulose, pullulan, agarose, etc., cross-linked with a polysaccharide, e.g., bisepoxide, epihalohydrin, or a lower hydrocarbon substituted with 1,2,3-trihal to provide suitable porosity and strength. In one embodiment, the solid support may be, but is not limited to, porous agarose beads. Solid supports as used herein can be prepared according to standard methods, such as inverse suspension gelatinization (S Hjerten: Biochem Biophys Acta 79 (2), 393-398 (1964)) or commercially available products, such as, but not limited to, Sepharose™ FF (Amersham Biosciences, Uppsala, Sweden).

In other example, the solid support may be based on synthetic polymers such as polyvinyl alcohol, polyhydroxyalkyl acrylate, polyhydroxyalkyl methacrylate, polyacrylamide, polymethacrylamide, and the like. In the case of hydrophobic polymers, such as matrices based on divinyl and monovinyl-substituted benzene, the surface of the matrix is often hydrophilized to expose hydrophilic groups as described above to the surrounding aqueous liquid. The polymer can be prepared according to standard methods (e.g. "Styrene based polymer supports developed by suspension polymerization", R. Arshady:Chimica eL'Industria 70 (9), 70-75 (1988)) or commercially available products can be used, such as, but not limited to, Source™) (Amersham Biosciences, Uppsala, Sweden).

In another example, the solid support may comprise a support of an inorganic nature, such as silica, zirconium oxide, or the like, or the solid support may be in another form, such as a surface, chip, capillary, or filter.

In one example, the matrix may be in the form of a porous monolith, or in the form of beads or particles, porous or non-porous. The beaded or particulate matrix may be used as a packed bed or in a suspended form. The suspended form includes what is known as an expanded bed and a pure suspension, in which the particles or beads can move freely. For monoliths, packed beds, and expanded beds, the separation process is typically after conventional chromatography via a concentration gradient.

The ligand (the polypeptide, the multimer thereof, immunoglobulin-binding protein, or protein L variant) can be attached to the support via conventional coupling techniques using, for example, amino and/or carboxy groups present on the ligand. Bisepoxide, epichlorohydrin, CNBr, N-hydroxysuccinimide (NHS), and others are well-known coupling agents. Between the support and the ligand, a molecule known as a spacer can be introduced, which will improve the utilization of the ligand and facilitate the chemical coupling of the ligand to the support. Alternatively, the ligand can be attached to the support by non-covalent binding, such as physical adsorption or biospecific adsorption.

Compared to conventional protein L-containing matrices used in affinity chromatography, the matrices provided herein may have an increase in binding capacity of about 5% or more, about 10% or more, about 15% or more, about 20% or more, about 25% or more, or about 30% or more to an immunoglobulin (e.g., IgG (IgG1, IgG2, IgG,3, or IgG4) or fragment comprising a light chain region thereof (e.g., scFv, Fab, etc.) in basic conditions (e.g., pH 9 or greater, pH 9.5 or greater, pH 10 or greater, pH 10.5 or greater, pH 11 or greater, pH 11.5 or greater, pH 12 or greater, pH 12.5 or greater, or pH 13 or greater; more specifically, washed 1 to 20 times (e.g. 15 times) with an alkaline solution (e.g., 0.3 M NaOH solution, about pH 13.48)), but are not limited thereto.

For Immunoglobulin Binding, Isolation, and Purification

Polypeptides (B3 domain variants), multimers, immunoglobulin-binding proteins, protein L variants, and/or one or more target compounds (e.g., proteins such as immunoglobulins) provided herein may be separated and/or purified from a liquid by adsorption onto a matrix for chromatography.

Another embodiment provides use for immunoglobulin binding and/or immunoglobulin isolation and/or purification of the polypeptide (B3 domain variant), multimer thereof, immunoglobulin-binding protein, protein L variant, and/or matrix for chromatography.

More specifically, one example provides a composition for immunoglobulin binding comprising at least one selected from the group consisting of the polypeptide (B3 domain variant), multimer, immunoglobulin-binding protein, protein L variant, nucleic acid molecule encoding them, recombinant vector and recombinant cell, and matrix for chromatography.

Another example provides a composition for the isolation and/or purification of an immunoglobulin comprising at least one selected from the group consisting of the polypeptide (B3 domain variant), multimer, immunoglobulin-binding protein, protein L variant, and matrix for chromatography.

In another embodiment, provided is a method of isolating and/or purifying an immunoglobulin, comprising the step of adsorbing the immunoglobulin by contacting a sample comprising the immunoglobulin with at least one selected from the group consisting of the polypeptide (B3 domain variant), multimer, immunoglobulin-binding protein, protein L variant, and matrix for chromatography.

Another example provides a method of isolating and/or purifying one or more target compounds from a liquid, comprising the step of adsorbing the target compound by contacting a liquid sample comprising a target compound with at least one selected from the group consisting of the polypeptide (B3 domain variant), multimer, immunoglobulin-binding protein, protein L variant, and matrix for chromatography.

As used herein, the immunoglobulin may be derived from a human, a primate such as a monkey, a rodent such as a mouse, a rat, or the like, and may be selected from various subtypes of IgG (IgG1, IgG2, IgG3, or IgG4), IgA, IgD, IgE, IgM, and the like. The immunoglobulin to be purified and/or isolated may be in its complete form or in a fragmented form including light chains, such as, but not limited to, scFv, Fab, $(scFv)_2$, Fab, Fab', or $F(ab')_2$.

The method of isolation and/or purification of the immunoglobulin or target compound may be chromatography, e.g., affinity chromatography.

Briefly describing the above affinity chromatography, in a first step, a solution comprising a target compound, e.g., an immunoglobulin or fragment thereof as described above (e.g., a cell culture expressing the immunoglobulin or fragment thereof, etc.) is passed through a separation matrix under conditions that allow the target compound to adsorb to a ligand present on the separation matrix. These conditions are controlled, for example, by pH and (or) salt concentration, i.e., the ionic strength of the solution. The capacity of the matrix must not be exceeded and for satisfactory adsorption the flow rate should be sufficiently slow. At this stage, the other components of the solution will, in principle, pass through without any obstruction. Although not required, the matrix is then washed, for example using an aqueous solution, to remove any retained and/or loosely bound material. The matrix provided in the present disclosure has the advantage of retaining its binding capacity to the target compound (e.g., immunoglobulin or fragment thereof) even after performing the washing step using an alkaline preparation. In the next step, a second solution, referred to as an eluent, is passed over the matrix under conditions that enable desorption, i.e. release, of the target compound. These conditions are typically provided by changes in pH, salt concentration, i.e. ionic strength, hydrophobicity, etc. Several elution methods are known, including gradient elution and stepwise elution. The elution can also be accomplished by a second solution including a competitor to replace the desired antibody on the matrix.

Effect of Invention

By providing an immunoglobulin-binding protein with improved alkaline tolerance and stability under alkaline conditions, the protein can be advantageously applied as an immunoglobulin-binding ligand in immunoglobulin purification techniques that essentially involve washing processes with alkaline preparations such as chromatography.

EXAMPLES

Figure 1:
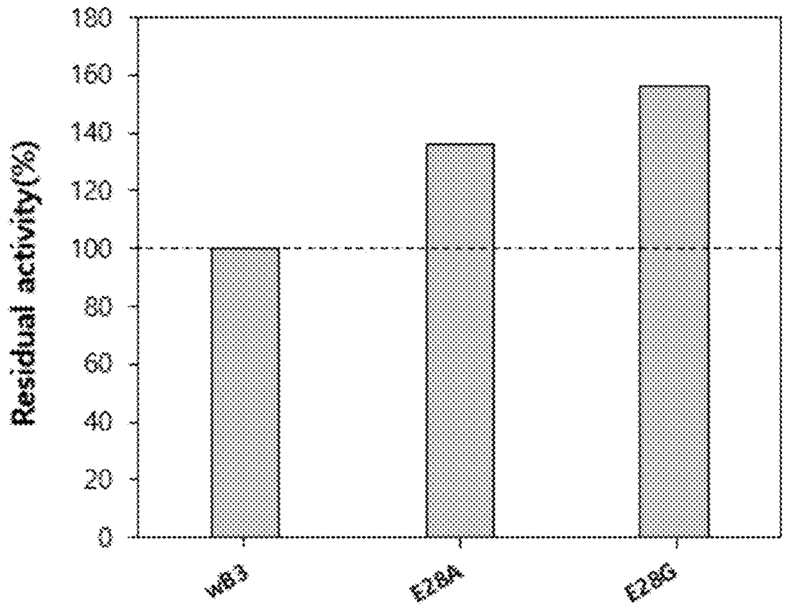
FIG. 1 is a graph showing scFv binding affinity (measured as absorbance) of B3 domain variants EP1 (E28A) and EP2 (E28G) after alkaline treatment compared to the wild type (wB3) according to an example (first error prone PCR results).

In the following, the invention is further described by way of example, which is by way of illustration only and is not intended to limit the scope of the invention. It will be apparent to those skilled in the art that the embodiments described below may be modified without departing from the essential spirit of the invention.

<Example 1> Preparation of Recombinant Immunoglobulin G Fragment (IgG(f)) Protein for Improvement <1-1> Synthesis of the IgG(f) Gene of Immunoglobulin G The nucleic acid sequence encoding a polypeptide (IgG (f); Herceptin scFv; SEQ ID NO: 2) of the human IgG1-based scFv region (IgG(f) gene; SEQ ID NO: 1) was found by Blast at the NCBI site (GenBank Accession No. AWW43726) and synthesized by CosmoGeneTech (Daejeon, Korea).

<1-2> Preparation of the pET-IgG(f) Plasmid

The pET-IgG(f) plasmid was prepared by inserting the IgG(f) gene obtained in Example <1-1> into the NdeI and XhoI restriction enzyme recognition sites of the pET29a(+) vector (Stratagene, USA). The details are as follows:

The IgG(f) gene DNA product (SEQ ID NO: 1) obtained through synthesis in Example <1-1> was cleaved with restriction enzymes NdeI and XhoI, purified with a purification kit (QIAEX Gel Extraction Kit; Qiagen, Germany), and used as insert DNA. In addition, the pET29a(+) vector DNA was cut with restriction enzymes NdeI and XhoI and dephosphorylated with antartic phosphatase (Genomics, Korea), and the resulting DNA fragment was used as a vector DNA. The insert DNA and vector DNA were ligated using T4 DNA ligase (Genomics, Korea) for 16 hours at 16° C., and the ligation solution was used to transform *E. coli* BL21(DE3) strain (Genomics) by electroporation. Transformants were selected by plating the above strain on LB agar medium containing kanamycin antibiotic at a concentration of 50 μg/mL and incubating it at 37° C. for 16-18 hours. By isolating the plasmid from these transformants and determining the sequence of the insert DNA, a pET-IgG(f) plasmid containing the IgG(f) gene with the nucleotide sequence of SEQ ID NO: 1 was prepared. The pET-IgG(f) plasmid expresses a wild-type IgG(f) protein (Herceptin scFv) represented by SEQ ID NO: 2.

<1-3> Purification of IgG(f) Protein Using Nickel-Affinity Resin

To seed the *E. coli* BL21(DE3) transformants containing the IgG(f) gene, 5 mL of LB liquid medium (BD (Becton, Dickinson and Company)) containing kanamycin antibiotic was dispensed into a 50 mL conical tube, inoculated with the selected transformants, and shaken for 16 hours at 37° C. and 200 rpm. A 500-mL triangular flask containing 200 mL of LB liquid medium was inoculated with 1% (v/v) of the above seed culture and agitated at 37° C., 200 rpm. After shaking to approximately OD600=0.6, IPTG (isopropyl-β-D-thio-galactopyranoside) was added to a final concentration of 1 mM and further agitated at 37° C., 200 rpm for 18 hours. The flask culture was centrifuged (4° C., 8,000 rpm, 20 min) to recover the bacteria, which were then suspended in 10 mL of PBS buffer (pH 7.4) (Intron Biotechnology, Korea). This suspension was disrupted with an ultrasonic grinder at 4° C. for 15 minutes and centrifuged (4° C., 20,000 rpm, 20 minutes) to obtain only the supernatant. 1 mL of WorkBeads™ 40 Ni-NTA (bioworks, Sweden), a nickel-affinity resin, was loaded onto the column, followed by 5 mL of binding buffer (20 mM NaH2PO4, 300 mM NaCl, 10 mM Imidazole pH 8.0), and 2.5 mL of the above supernatant was mixed with 2.5 mL of binding buffer and loaded onto the column. 5 mL of wash buffer (20 mM NaH2PO4, 300 mM NaCl, 30 mM Imidazole pH 8.0) was added, followed by 2.5 mL of elution buffer (20 mM $NaH_2PO_4$, 300 mM NaCl, 300 mM Imidazole pH 8.0), and the passage was collected in a 15 mL conical tube. The recovered purified protein was desalted using a HiPrep 26/10 desalting column (cytiva, Sweden).

<Example 2> Create a Template

<2-1> B3 Domain Gene Synthesis

The B3 domain gene (SEQ ID NO: 3) of *Peptostreptococcus magnus*-derived protein L was synthesized by including a 6×His tag by CosmoGeneTech (Daejeon, Korea).

<2-2> Preparation of the pBC-wB3 Plasmid

The wild-type B3 domain (wB3) gene (SEQ ID NO: 3) of protein L obtained in Example 2-1 above was inserted into the NdeI and NotI restriction enzyme recognition sites of the pBC KS(+) vector (Stratagene, USA) to prepare the pBC-wB3 plasmid. In detail, the procedure was as follows:

The wB3 gene DNA product (SEQ ID NO: 3) obtained by synthesis in Example <2-1> was cleaved with restriction enzymes NdeI and NotI, purified with a purification kit (QIAEX Gel Extraction Kit; Qiagen, Germany), and used as insert DNA. In addition, the pBC KS(+) vector DNA was cleaved with restriction enzymes NdeI and NotI, and the DNA fragment dephosphorylated with antisense phosphatase (Genomics, Korea) was used as a vector DNA. The insert DNA and vector DNA were ligated using T4 DNA ligase (Genomics, Korea) for 16 hours at 16° C., and the ligation solution was used to transform *E. coli* DH5α strain (Genomics) by electroporation. The above strains were plated on LB agar medium (BD (Becton, Dickinson and Company)) containing chloramphenicol antibiotic at a concentration of 20 μg/mL, and transformants were screened by subculturing at 37° C. for 16-18 hours. The plasmid was isolated from the selected transformants and the sequence of the insertion DNA was determined, resulting in the preparation of a pBC-wB3 plasmid containing the wild-type B3 domain gene with the nucleotide sequence of SEQ ID NO: 3. The pBC-wB3 plasmid expresses the wild-type protein L B3 domain protein represented by SEQ ID NO: 4.

<Example 3> Improvement of wB3 Using Error Prone Polymerase Chain Reaction (PCR)

<3-1> Preparation of wB3 Variant Library by Error Prone Polymerase Chain Reaction (PCR)

To artificially induce random mutations in the nucleic acid sequence of the wB3 gene (SEQ ID NO: 3) synthesized in Example 2, an error prone polymerase chain reaction (PCR) was carried out to construct a mutant library.

Specific mutant libraries were prepared as follows: Error-induced polymerase chain reaction was carried out using the Diversity® PCR Random Mutagenesis kit (Clontec, USA) to generate 1-2 mutations per 1000 bp. The composition of the PCR reaction mixture was 1 ng of pBC-wB3 plasmid (Examples 2-2) as a template DNA, 10 pmol each of EP-F primer (SEQ ID NO: 5) and T7 primer (SEQ ID NO: 6), 40 μM dGTP, Diversity dNTP mix and TITANIUM™ Taq DNA polymerase, adjusted to a final volume of 100 μL. PCR was performed under the following conditions using a C1000 Touch thermal cycler (BIO-RAD, USA): The reaction mixture was pre-denatured at 94° C. for 30 s, followed by denaturation at 94° C. for 30 s, annealing at 55° C. for 30 s, and polymerization at 68° C. for 3 mins, and the reaction was repeated 16 times, followed by post-polymerization at 68° C. for 1 min.

Each wB3 mutant gene PCR product obtained by the error-induced polymerase chain reaction performed under the above conditions was digested with restriction enzymes NdeI and NotI, purified by QIAEX Gel Extraction Kit (Qiagen, Germany), and used as insert DNA. In addition, the pBC-KS(+) plasmid was digested with restriction enzymes NdeI and NotI, and a 3.4-kb DNA fragment dephosphorylated with antartic phosphatase (Genomics, Korea) was used as a vector DNA. The insert DNA and vector DNA were ligated using T4 DNA ligase (Genomics, Korea) at 16° C. for 16 hours, and the ligation solution was used to transform *E. coli* DH5α strain by electroporation. Random mutant libraries were prepared by plating the above strains on LB agar medium containing chloramphenicol antibiotic at a concentration of 20 μg/mL and culturing them at 37° C. for 16-18 hours.

<3-2> Selecting Variants with Increased Alkali Tolerance

To culture the *E. coli* DH5α transformants including the wB3 mutant gene induced by the above method, 500 μL of LB liquid medium containing chloramphenicol antibiotic was dispensed into 96-deep well plates (Bionia, Korea), the transformants were inoculated, and the plates were shaken for 18 hours at 37° C. and 280 rpm.

The specific protein purification procedure was as follows:

Protein purification was performed by using a Promega HisLink™ 96 Protein Purification System (Promega, USA). 10× FastBreak™ Cell Lysis Reagent and DNase I solution were mixed proportionally to prepare FastBreak™ Reagent/DNase I solution. 600 μL of culture medium and 60 μL of FastBreak™ Reagent/DNase I solution was added to each well, followed by adding 65 μL of HisLink™ Resin. The mixture was mixed for 30 minutes at 100 rpm on a shaker to allow the culture and resin to react. The reaction solution and resin were transferred to a filtration plate and filtered by applying vacuum for 10 s using a Vac-Man® 96 Vacuum Manifold (Promega, USA). Next, 250 μL of binding/wash buffer (100 mM HEPES, 10 mM imidazole, pH 7.5) was added to each well and washed under vacuum for 10 s. The same method was repeated three times. 200 μL of elution buffer (100 mM HEPES, 500 mM imidazole, pH 7.5) was added to the plate and reacted for 10 minutes, followed by 1 minute of vacuum to recover the purified protein in a new 96-well plate. The purified wB3 variants were coupled to N-hydroxysuccinimide (NHS)-Activated sepharose 4 Fast flow (Cytiva, Sweden) on the 96-well plate and transferred to a filtration plate. 150 μL (71.5 μg/mL) of the IgG(f) protein purified in Examples <1-3> was added to the filtration plate and reacted for 1 hr at 100 rpm at room temperature using a shaker. The unbound IgG(f) protein was removed by vacuum, and then 150 μL of PBS buffer (pH 7.4) was added to each well, washed by vacuum, and washed three times in the same manner. 150 μL of elution buffer (0.1 M Glycine-HCl, pH 2.5) was added and reacted for 30 seconds at room temperature, followed by 1 minute of vacuum to recover the protein in a new 96-well plate. The filtration plate that had been treated with elution buffer was washed by dispensing 150 μL of PBS buffer into each well and applying vacuum, and was washed three times in the same manner.

New 96-well plates with recovered proteins were transferred and the amount of IgG(f) protein was measured at OD280 using a Synergy HTX multi-mode reader (BioTek, USA). After the initial binding assay, to confirm the alkaline tolerance of the wB3 variants, 200 μL of 0.3M NaOH (pH 13.48) was added to the wB3 variant resin in the filtration plate and reacted at 100 rpm for 1 h at room temperature. The plate was then washed three times with 200 μL of PBS buffer, and the IgG(f) protein was bound and recovered in the same manner as the initial binding assay to measure the amount of antibody. The residual IgG(f) binding activity of the wB3 variants was analyzed by repeating the same method as above and comparing the amount of IgG(f) protein remaining.

By comparing the absorbance of the above wB3 variants before and after 0.3 M NaOH treatment, two wB3 variants with increased alkali tolerance were selected.

The two selected variants were confirmed by nucleic acid sequencing of their genes, which revealed that wild-type wB3 (SEQ ID NO: 4) was mutated into variant EP1 (SEQ ID NO: 7) with E28A mutation (refers to a variant in which the 28th (i.e., 29th in SEQ ID NO: 4) amino acid residue, E, is substituted with A, starting from the amino acid residue following the methionine (M) encoded by the initiation codon (i.e., P, the second amino acid residue in SEQ ID NO: 4) upon recombinant synthesis; in the present specification, amino acid variant designations are interpreted in the same manner) and variant EP2 (SEQ ID NO: 8) with E28G mutation. The absorbance of the two selected variants EP1 (E28A) and EP2 (E28G) compared to the absorbance of the wild type (wB3) is shown in FIG. 1 (expressed as a relative value to the absorbance of wB3 (100%)).

<3-3> Construction of EP2 Variant Library by Error Prone Polymerase Chain Reaction (PCR)

Among the wB3 variants selected in Example <3-2>, the gene coding for EP2 (E28G) (SEQ ID NO: 8), a variant with higher alkali tolerance, was further improved. An error prone polymerase chain reaction (PCR) was performed once more by inserting EP2 into the pBC KS(+) vector as a new template.

Figure 2:
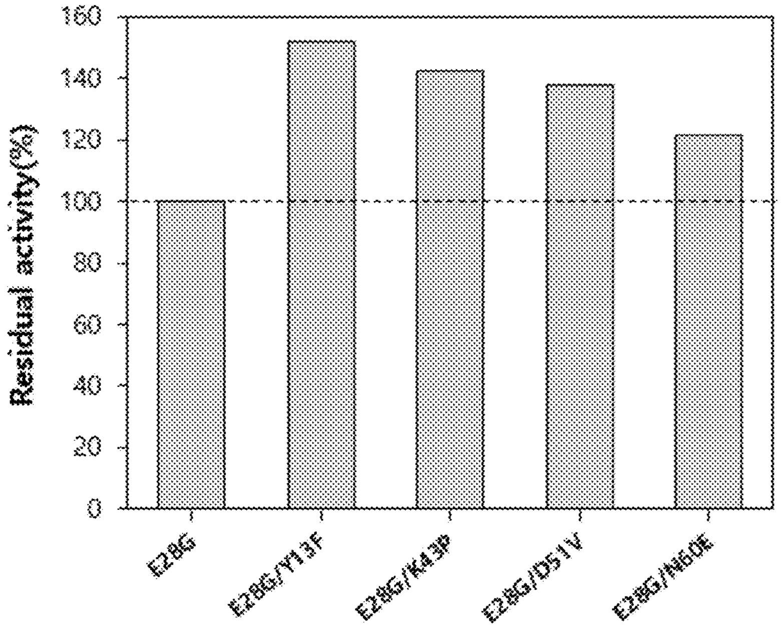
FIG. 2 is a graph showing scFv binding affinity (measured as absorbance) of four B3 domain variants BEP1 (E28G/Y13F), BEP2 (E28G/K43P), BEP3 (E28G/D51V), and BEP4 (E28G/N60E) after alkali treatment compared to variant EP2 (E28G) (100%) according to an example (second error prone PCR results).

Proteins with increased alkali tolerance than EP2 were selected by error-induced polymerase chain reaction using the same method as in Examples <3-1> and <3-2>. As a result, four additional variants were selected, and nucleic acid sequencing of their genes confirmed that variant EP2 mutated into variant BEP1 (SEQ ID NO: 9) with an E28G/Y13F mutation, variant BEP2 (SEQ ID NO: 10) with an E28G/K43P mutation, variant BEP3 (SEQ ID NO: 11) with an E28G/D51V mutation, and variant BEP4 (SEQ ID NO: 12) with an E28G/N60E mutation. The absorbance of the four identified variants BEP1(E28G/Y13F), BEP2(E28G/K43P), BEP3(E28G/D51V), and BEP4(E28G/N60E) compared to the absorbance of variant EP2(E28G) is shown in FIG. 2 (expressed as a relative value to the absorbance of EP2 (100%)).

<Example 4> Improvement of wB3 Using Site-Saturation Mutagenesis

<4-1> Construction of wB3 Variant Library by Site-Directed Mutagenesis

To confer additional alkali tolerance to the EP2 (E28G) gene modified from the wB3 gene, a site-saturation mutagenesis library was constructed for the five amino acid residues (Y13, E28, K43, D51, N60) mutated in the selected variants in Example 3. The specific methods were as follows:

To prepare the library with the modified 28th amino acid (corresponding to the 29th amino acid of SEQ ID NO: 4 comprising a methionine (M) by initiation codon at the N-terminus; in the present specification, amino acid position indications are interpreted in the same manner), the wB3 gene (SEQ ID NO: 3) inserted into the pBC KS(+) vector was used as a template, and the reaction mixture was prepared with 28-F primer (SEQ ID NO: 13), 28-R primer (SEQ ID NO: 14), Pfu-X DNA polymerase, 10×Pfu-X Reaction buffer, and 10 mM dNTPs, adjusting the final volume to 50 μL. The reaction mixture was reacted under the following reaction conditions: pre-denaturation at 95° C. for 2 min, followed by denaturation at 95° C. for 20 s, annealing at 56° C. for 40 s and polymerization at 72° C. for 1 min, the reaction was repeated 25 times followed by post-polymerization at 72° C. for 5 min. The PCR products obtained under the above conditions were treated with the restriction enzyme DpnI for 18 hours, purified with a PCR purification kit (Cosmozintec, Korea), and immediately transformed into *E. coli* DH5α strain by electroporation. The transformed strain was plated on LB agar medium containing chloramphenicol antibiotic at a concentration of 20 μg/mL and subcultured at 37° C. for 16-18 hours to prepare a positional saturation mutant library.

Then, using the same method as described above, using the BEP1 (SEQ ID NO: 9) coding gene, the BEP2 (SEQ ID NO: 10) coding gene, the BEP3 (SEQ ID NO: 11) coding gene, or the BEP4 (SEQ ID NO: 12) coding gene inserted in the pBC KS(+) vector as a template, library were constructed using 13-F primer (SEQ ID NO: 15) and 13-R primer (SEQ ID NO: 16), 43-F primer (SEQ ID NO: 17) and 43-R primer (SEQ ID NO: 18), 51-F primer (SEQ ID NO: 19) and 51-R primer (SEQ ID NO: 20), 60-F primer (SEQ ID NO: 21) and 60-R primer (SEQ ID NO: 22), respectively.

<4-2> Selecting Variants with Increased Alkali Tolerance

Figure 3:
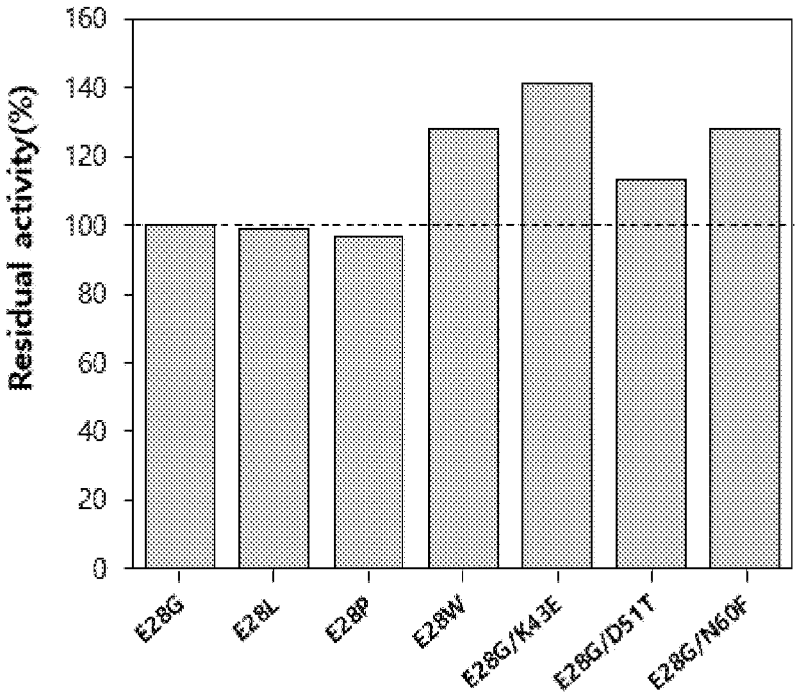
FIG. 3 is a graph showing scFv binding affinity (measured as absorbance) of six B3 domain variants EPS1 (E28L), EPS2 (E28P), EPS3 (E28W), EPS4 (E28G/K43E), EPS5 (E28G/D51T), and EPS6 (E28G/N60F) after alkali treatment compared to variant EP2 (E28G) according to an example (third error prone PCR results).

Using the same method as described in Example <3-2>, the library produced in Example <4-1> was studied. Six additional variants EPS1(E28L) (SEQ ID NO: 23), EPS2 (E28P) (SEQ ID NO: 24), EPS3(E28W) (SEQ ID NO: 25), EPS4(E28G/K43E) (SEQ ID NO: 26), EPS5(E28G/D51T) (SEQ ID NO: 27), and EPS6(E28G/N60F) (SEQ ID NO: 28) were further selected as variants with equal or increased alkali tolerance compared to variant EP2(E28G). The absorbance of these six additional selected variants was compared to the absorbance of variant EP2 (E28G), and the results are shown in FIG. 3 (expressed as a relative value to the absorbance of EP2 (100%)).

<Example 5> Improvement of wB3 Using DNA Shuffling

Figure 4:
FIG. 4 is a schematic illustrating an exemplary process for creating a positional mutant library for selection of variants with an increased alkali tolerance.

Additional alkali tolerance to the variants with increased alkali tolerance identified in Examples 3 and 4 were conferred through DNA shuffling. For this purpose, DNA shuffling library was constructed for the five selected amino acid variants (Y13F, E28G/W, K43E/P, D51T/V, and N60E/F). The specific procedure was as follows (see FIG. 4):

First, to prepare a library in which the 13th amino acid was mutated, the EP2 (E28G) (SEQ ID NO: 8) coding gene was used as a template, and PCR was performed using the EP-F primer (SEQ ID NO: 5), SH13-R1 primer (SEQ ID NO: 31), and SH13-R2 primer (SEQ ID NO: 32) to recover a PCR product of approximately 0.1 kb in size. To prepare a library in which the 28th amino acid was mutated, the gene encoding wB3 (SEQ ID NO: 4), the gene encoding EP2 (E28G) (SEQ ID NO: 8), and the gene encoding EPS3 (SEQ ID NO: 25) were used as template, and PCR was performed using SH13-F1 primer (SEQ ID NO: 29), SH13-F2 primer (SEQ ID NO: 30), SH43-R1 primer (SEQ ID NO: 35), and SH43-R2 primer (SEQ ID NO: 36) to recover a PCR product of approximately 0.14 kb in size. To prepare a library in which the 43rd amino acid was mutated, the EP2 (E28G) (SEQ ID NO: 8) coding gene was used as a template and PCR was performed using the SH43-F1 primer (SEQ ID NO: 33), SH43-F2 primer (SEQ ID NO: 34), SH51-R1 primer (SEQ ID NO: 39), and SH51-R2 primer (SEQ ID NO: 40) to recover a PCR product of approximately 0.07 kb in size. To prepare a library in which the 51st amino acid was mutated, the EP2 (E28G) (SEQ ID NO: 8) coding gene was used as a template and PCR was performed using the SH51-F1 primer (SEQ ID NO: 37), SH51-F2 primer (SEQ ID NO: 38), SH60-R1 primer (SEQ ID NO: 44), SH60-R2 primer (SEQ ID NO: 45), and SH60-R3 primer (SEQ ID NO: 46) to recover a PCR product of approximately 0.08 kb in size. To prepare a library in which the 60th amino acid was mutated, the EP2 (E28G) (SEQ ID NO: 8) coding gene was used as a template, and PCR was performed using the SH60-F1 primer (SEQ ID NO: 41), SH60-F2 primer (SEQ ID NO: 42), SH60-F3 primer (SEQ ID NO: 43), and T7 primer (SEQ ID NO: 6) to recover a PCR product of approximately 0.32 kb in size. The composition of the PCR reaction solution was prepared by adjusting the final volume to 100 μL with the respective template DNA, primers, Pfu-X DNA polymerase, 10×Pfu-X Reaction buffer, and 10 mM dNTPs. The above reaction mixture was reacted under the following conditions: pre-denaturation at 95° C. for 2 min, followed by denaturation at 95° C. for 50 secs, annealing at 58° C. for 40 secs and polymerization at 72° C. for 1 min, the reaction was repeated 25 times and post-polymerization at 72° C. for 5 min.

A PCR product of 102 bp, a PCR product of 141 bp, a PCR product of 67 bp, a PCR product of 78 bp, and a PCR product of 320 bp obtained under the above conditions were mixed and PCR was performed without adding primers to recover a PCR product of about 0.7 kb in size consisting of five PCR products ligated together. Using the above PCR product of about 0.7 kb as a template, PCR was performed using EP-F primer (SEQ ID NO: 5) and T7 primer (SEQ ID NO: 6) to amplify a multi-variant DNA fragment of about 0.7 kb in size. The PCR product of about 0.7 kb was inserted into the pBC KS(+) vector DNA in the same manner as in Example <2-2>, and transformation of the *E. coli* DH5α strain was performed to prepare a DNA shuffling library.

over time was measured by the same method as in Example 3 to compare the alkali tolerance. The absorbance over time obtained is shown in FIG. 5 as a relative value to the absorbance (100%) at the beginning (0 h).

Figure 5:
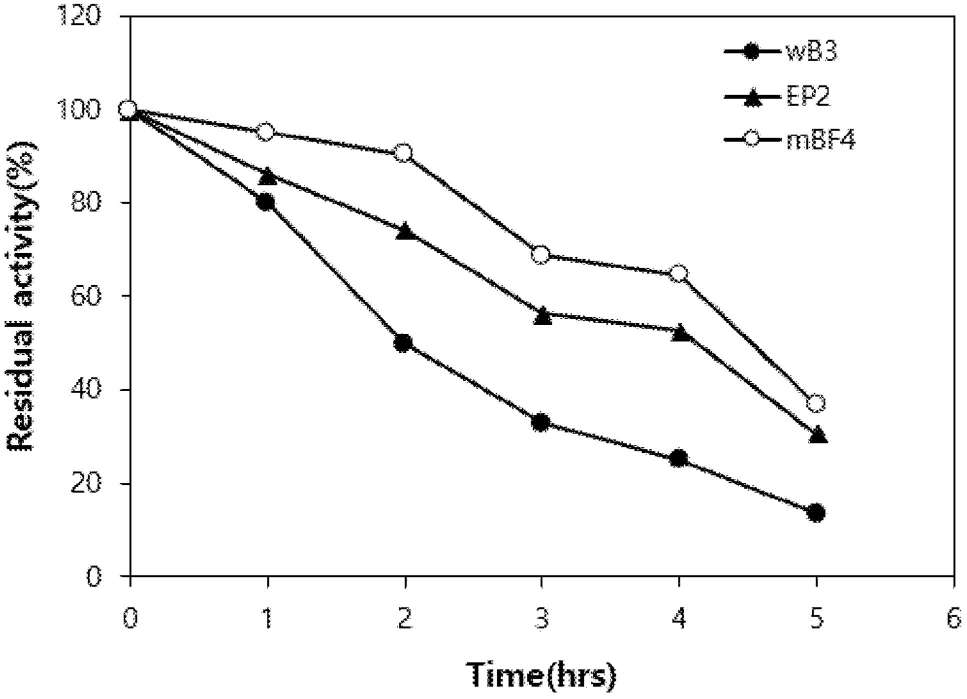
FIG. 5 is a graph showing a change in scFv binding affinity (measured as absorbance) over time following alkaline treatment of the B3 domain variant mBF4 (Y13F/E28G/K43P) compared to the wild-type B3 domain according to an example.

As shown in FIG. 5, the library of Example 5 was explored using the same method as in Examples <3-2>, and mBF4 (Y13F/E28G/K43P) (SEQ ID NO: 47) was selected as a variant with increased alkali tolerance compared to variant EP2. As shown in FIG. 5, the mBF4 protein exhibited an approximately 2.7-fold increase in alkali tolerance compared to the wB3 protein with the wild-type amino acid sequence when comparing activity after 5 hours of treatment in 0.3 M NaOH.

The amino acid sequences of the protein L B3 domain variants selected in Examples 1 to 6 above are summarized in Table 2 below:

TABLE 2

| SEQ ID NO: | Description | Sequence (N→C) |
|---|---|---|
| 4 | Wild-type Protein L B3 domain | MPKEEVTIKANLIYADGKTQTAEFKGTFEEATAEAYR<br>YADLLAKENGKYTVDVADKGYTLNIKFAGKEKTPEE |
| 7 | Protein L B3 domain variant EP1 (E28A) | MPKEEVTIKANLIYADGKTQTAEFKGTFAEATAEAYR<br>YADLLAKENGKYTVDVADKGYTLNIKFAGKEKTPEE |
| 8 | Protein L B3 domain variant EP2 (E28G) | MPKEEVTIKANLIYADGKTQTAEFKGTFGEATAEAYR<br>YADLLAKENGKYTVDVADKGYTLNIKFAGKEKTPEE |
| 9 | Protein L B3 domain variant BEP1 (E28G/Y13F) | MPKEEVTIKANLIFADGKTQTAEFKGTFGEATAEAYR<br>YADLLAKENGKYTVDVADKGYTLNIKFAGKEKTPEE |
| 10 | Protein L B3 domain variant (E28G/K43P) | MPKEEVTIKANLIYADGKTQTAEFKGTFGEATAEAYR<br>YADLLAPENGKYTVDVADKGYTLNIKFAGKEKTPEE |
| 11 | Protein L B3 domain variant BEP3 (E28G/D51V) | MPKEEVTIKANLIYADGKTQTAEFKGTFGEATAEAYR<br>YADLLAKENGKYTVVVADKGYTLNIKFAGKEKTPEE |
| 12 | Protein L B3 domain variant BEP4 (E28G/N60E) | MPKEEVTIKANLIYADGKTQTAEFKGTFGEATAEAYR<br>YADLLAKENGKYTVDVADKGYTLEIKFAGKEKTPEE |
| 23 | Protein L B3 domain variant EPS1 (E28L) | MPKEEVTIKANLIYADGKTQTAEFKGTFLEATAEAYR<br>YADLLAKENGKYTVDVADKGYTLNIKFAGKEKTPEE |
| 24 | Protein L B3 domain variant EPS2 (E28P) | MPKEEVTIKANLIYADGKTQTAEFKGTFPEATAEAYR<br>YADLLAKENGKYTVDVADKGYTLNIKFAGKEKTPEE |
| 25 | Protein L B3 domain variant EPS3 (E28W) | MPKEEVTIKANLIYADGKTQTAEFKGTFWEATAEAYR<br>YADLLAKENGKYTVDVADKGYTLNIKFAGKEKTPEE |
| 26 | Protein L B3 domain variant EPS4 (E28G/K43E) | MPKEEVTIKANLIYADGKTQTAEFKGTFGEATAEAYR<br>YADLLAEENGKYTVDVADKGYTLNIKFAGKEKTPEE |
| 27 | Protein L B3 domain variant EPS5 (E28G/D51T) | MPKEEVTIKANLIYADGKTQTAEFKGTFGEATAEAYR<br>YADLLAKENGKYTVTVADKGYTLNIKFAGKEKTPEE |
| 28 | Protein L B3 domain variant EPS6 (E28G/N60F) | MPKEEVTIKANLIYADGKTQTAEFKGTFGEATAEAYR<br>YADLLAKENGKYTVDVADKGYTLFIKFAGKEKTPEE |
| 47 | Protein L B3 domain variant mBF (Y13F/E28G/K43P) | MPKEEVTIKANLIFADGKTQTAEFKGTFGEATAEAYR<br>YADLLAPENGKYTVDVADKGYTLNIKFAGKEKTPEE |

<Example 6> Development of mBF Variants with Increased Alkaline Tolerance: Comparison of Alkaline Tolerance of Variant Protein mBF Monomers The library prepared in Example 5 was purified by the same manner as in Examples <1-3>, and the absorbance

<Example 7> Alkali Tolerance of mBF Tetramers

<7-1> Synthesizing the 4mBF Gene

To further confirm the alkali tolerance of the mBF4 protein identified in Example 6-1, the gene encoding the mBF4 variant was synthesized as a tetramer and named 4mBF. The gene sequence was synthesized by Cosmo-GeneTech (Daejeon, Korea) after codon optimization (SEQ ID NO: 48).

<7-2> Preparation of pET-4mBF Plasmid

The 4mBF gene (SEQ ID NO: 48) obtained in the above Example <7-1> was cloned into the pET29a(+) vector (Stratagene, USA) as described in Example <1-2> to prepare a pET-4mBF plasmid. The pET-4mBF plasmid expressed a variant protein 4mBF represented by SEQ ID NO: 49.

<7-3> Purification of Variant Protein mBF Tetramers Using Nickel-Affinity Resin

To seed the *E. coli* DH5α transformants transformed with the pET-4mBF plasmid and containing the 4mBF gene, 5 mL of LB liquid medium containing kanamycin antibiotic was dispensed into a 50 mL conical tube, the selected transformants were inoculated, and the culture was shaken for 16 hours at 37° C. and 200 rpm. 500 mL of TB liquid medium containing kanamycin antibiotic was dispensed into a 2000 mL triangular flask, inoculated with 1% (v/v) of the selected transformants, and shaken at 37° C., 200 rpm. After shaking to approximately OD600=0.6, isopropyl-β-D-thio-galactopyranoside (IPTG) was added to a final concentration of 1 mM and further shaken at 37° C., 200 rpm for 18 hours. The flask culture was centrifuged (4° C., 8,000 rpm, 20 min) to recover the bacteria and suspended in 30 mL of PBS buffer (pH 7.4) (Intron Biotechnology, Korea). This suspension was disrupted with an ultrasonic grinder at 4° C. for 30 minutes and centrifuged (4° C., 20,000 rpm, 20 min) to obtain only the supernatant. The column was loaded with 7 mL of WorkBeads™ 40 Ni-NTA (bioworks, Sweden), followed by 35 mL of binding buffer (20 mM $NaH2PO_4$, 300 mM NaCl, 10 mM Imidazole pH 8.0), mixed with 30 mL of the above supernatant and 30 mL of binding buffer, and loaded onto the column. 35 mL of wash buffer (20 mM $NaH_2PO_4$, 300 mM NaCl, 30 mM Imidazole pH 8.0) was run, followed by 40 mL of elution buffer (20 mM $NaH_2PO_4$, 300 mM NaCl, 300 mM Imidazole pH 8.0), and the passage was collected in a 50 mL conical tube. The purified protein was desalted using a HiPrep 26/10 desalting column (cytiva, USA).

<7-4> Comparison of Alkali Tolerance of Variant Protein mBF Tetramers

The 4mBF purified in Example <7-3> was coupled to N-hydroxysuccinimide (NHS)-Activated sepharose 4 Fast flow (Cytiva, Sweden). The prepared 4 mBF resin (4mBF-agarose bead) was compared for alkali tolerance to a commercially available protein L-based resin (Cytiva 17-5478-01, Capto L), which is known to be highly alkali-tolerant. A Tricorn 5/50 column (cytiva, USA) was loaded with 1 ml of each resin followed by 5 ml of PBS buffer (pH 7.4) (Intron Biotechnology, Korea) at 1 ml/min. 25 ml of approximately 1 mg/ml of purified antibody (KBIO, Korea) was diluted with 25 ml of PBS buffer and flowed at 1 ml/min. After removing unbound antibody protein by flowing 5 ml of PBS buffer at 1 ml/min, 5 ml of elution buffer (0.1 M Glycine-HCl, pH 2.5) was flowed at 0.5 ml/min and the passage liquid was collected to separate the bound antibody. The isolated antibody was then collected in a tube containing 0.5 ml of neutralization buffer (1 M Tris-HCl, pH 8.5) so that it could be neutralized, and the amount of recovered antibody was measured. After the initial binding assay, 5 ml of PBS buffer was flowed at 1 ml/min for alkaline treatment, followed by 7.5 ml of 0.3 M NaOH at 0.5 ml/min to allow the NaOH to contact the resin for 15 minutes. Then, 5 ml of PBS buffer was added at 1 ml/min to remove the remaining NaOH, which was set as one alkali treatment, and the alkali treatment was repeated in the same manner (1-15 cycles). After alkali treatment, the purified antibody was bound by the same method as the initial binding assay, and the amount of antibody was recovered and measured. The alkali tolerance of each resin was analyzed by repeating the above method and comparing the amount of antibody recovered.

Figure 6:
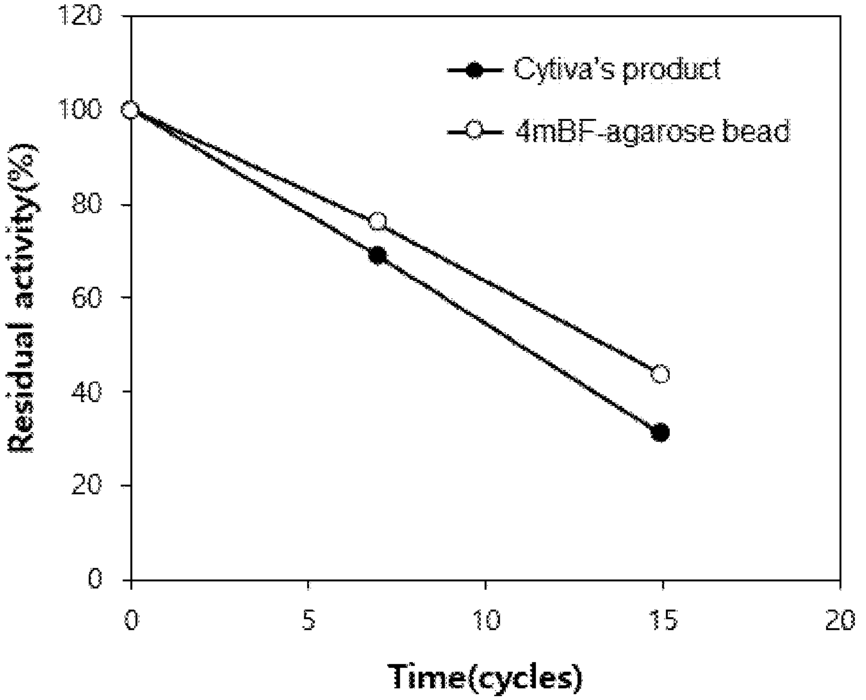
FIG. 6 is a graph showing s change in scFv binding affinity (measured as absorbance) following alkaline treatment (washing) cycles of tetrameric 4 mBF comprising the B3 domain variant mBF4 (Y13F/E28G/K43P) according to an example, compared to a commercially available product (Cytiva 17-5478-01, Capto L).

The results obtained above are shown in FIG. 6. As shown in FIG. 6, it was confirmed that the 4 mBF resin has excellent alkali tolerance compared to Cytiva's product, which is already widely used in industrial applications. In particular, when the alkali treatment was carried out up to 15 times, the residual activity of 4 mBF resin was 43.46%, which is about 1.4 times higher than that of Cytiva's product.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A polypeptide comprising SEQ ID NO:4, wherein the first amino acid (Met, M) is optionally absent, and wherein beginning from a proline (Pro, P) which is the second amino acid in the amino acid sequence of SEQ ID NO: 4, the 28th amino acid (glutamic acid (Glu, E)), is substituted with an amino acid selected from the group consisting of glycine (Gly, G), alanine (Ala, A), leucine (Leu, L), proline (Pro, P), and tryptophan (Trp, W).

2. The polypeptide of claim 1, further comprising at least one substitution selected from the group consisting of the following:

the 43rd amino acid (K) is replaced with proline (Pro, P) or glutamic acid (Glu, E);

the 13th amino acid (Y) is replaced with phenylalanine (Phe, F);

the 51st amino acid (D) is replaced with valine (Val, V) or threonine (Thr, T); and the 60th amino acid (N) is replaced with phenylalanine (Phe, F).

3. The polypeptide of claim 2, comprising the following amino acid substitutions in the amino acid sequence SEQ ID NO: 4: E28G+Y13F, E28G+K43P, E28G+D51V, E28G+N60E, E28G+K43E, E28G+D51T, E28G+N60F, or Y13F+E28G+K43P.

4. The polypeptide of claim 1, represented by the amino acid sequence of SEQ ID NO: 7, 8, 9, 10, 11, 12, 23, 24, 25, 26, 27, 28, or 47.

5. The polypeptide of claim 1, further comprising at least one selected from the group consisting of the A, B1, B2, B4, C, W, and M domain of protein L.

6. The polypeptide of claim 1, wherein the polypeptide has increased alkali tolerance relative to the polypeptide of SEQ ID NO: 4.

7. A multimer, comprising at least two repeating units of the polypeptide of claim 1.

8. The multimer of claim 7, represented by the amino acid sequence of SEQ ID NO: 49.

9. The multimer of claim 7, further comprising at least one selected from the group consisting of the A, B1, B2, B4, C, W, and M domain of protein L.

10. A protein L variant, comprising the polypeptide of claim 1, or a multimer comprising at least two repeating units of the polypeptide, as a B3 domain.

11. A nucleic acid molecule encoding the polypeptide of claim 1, a multimer comprising at least two repeating units of the polypeptide, or a protein L variant comprising the polypeptide or the multimer as a B3 domain.

12. A recombinant vector comprising the nucleic acid molecule of claim 11.

13. A recombinant cell comprising the nucleic acid molecule of claim 11 or a recombinant vector comprising the nucleic acid molecule.

14. A matrix for chromatography, wherein the polypeptide of claim 1, a multimer comprising at least two repeating units of the polypeptide, or a protein L variant comprising the polypeptide or the multimer as a B3 domain, is coupled to a solid support.

15. A composition for binding an immunoglobulin, comprising at least one selected from the group consisting of (1) the polypeptide of claim 1, (2) a multimer comprising two or more repeating units of the polypeptide, (3) a protein L variant comprising the polypeptide or the multimer as a B3 domain, (4) a nucleic acid molecule encoding the polypeptides, the multimer, or the protein L variant, (5) a recombinant vector comprising the nucleic acid molecule, (6) a recombinant cell comprising the nucleic acid molecule or a recombinant vector; and (7) a matrix for chromatography, wherein the polypeptide, the multimer, or the protein L variant is coupled to a solid support.

16. A composition for immunoglobulin isolation or purification, comprising (a) the polypeptide of claim 1, (b) a multimer comprising two or more repeating units of the polypeptide, (c) a protein L variant comprising the polypeptide or the multimer as a B3 domain; or (d) a matrix for chromatography, wherein a plurality of ligands comprising the polypeptides, multimer, or protein L variant are coupled to a solid support.

17. A method of isolating or purifying an immunoglobulin, comprising, adsorbing an immunoglobulin by contacting a sample comprising the immunoglobulin with at least one selected from the group consisting of the following:

(a) the polypeptide of claim 1, (b) a multimer comprising two or more repeating units of the polypeptide, (c) a protein L variant comprising the polypeptide or the multimer as a B3 domain; and (d) a matrix for chromatography, wherein a plurality of ligands comprising the polypeptides, the multimer, or the protein L variant are coupled to a solid support.

18. A method of isolating or purifying at least one target compound from a liquid comprising adsorbing the target compound by contacting a sample comprising the target compound with at least one selected from the group consisting of the following:

(a) the polypeptide of claim 1, (b) a multimer comprising two or more repeating units of the polypeptide, (c) a protein L variant comprising the polypeptide or the multimer as a B3 domain; and (d) a matrix for chromatography, wherein a plurality of ligands comprising the polypeptides, the multimer, or the protein L variant are coupled to a solid support.

* * * * *

SEQUENCE LISTING

```
Sequence total quantity: 50
SEQ ID NO: 1            moltype = DNA  length = 756
FEATURE                 Location/Qualifiers
misc_feature            1..756
                        note = Synthetic_Herceptin scFv coding nucleic acid sequence
source                  1..756
                        mol_type = other DNA
                        organism = synthetic construct
SEQUENCE: 1
aagcttgata ttcagatgac ccagagcccg tccagcctgt cagcaagcgt tggcgaccgt  60
gttacgatta cctgccgtgc ctcgcaagat gtgaacaccg cggtggcctg gtatcagcaa  120
aaaccgggca aagcaccgaa actgctgatt tatagtgctt cctttctgta ctctggtgtt  180
ccgtcccgtt tctcaggctc gcgcagcggt accgatttta ccctgacgat cagctctctg  240
cagccggaag acttcgccac gtattactgc cagcaacact acacgacccc gccgaccttc  300
ggccagggca ccaaagtgga aatcaaaggc gccagcggcg gtggcggttc tggtggcggt  360
ggcagcggtg gcggtggctc aagcgaagtc caactggtcg aatcgggtgg tggtctggtt  420
cagccgggcg gttcactgcg tctgtcgtgt gctgcctcgg gtttcaacat caaagatacc  480
tatattcatt gggtgcgtca ggccccgggt aaaggtctgg aatgggttgc ccgcatctac  540
ccgaccaacg gctatacgcg ttacgccgat agcgttaaag gtcgctttac catttctgca  600
gacaccagta aaaacacggc ttatctgcag atgaactctc tgcgtgcgga agacacggcc  660
gtgtattact gcagtcgctg gggcggtgat ggcttttatg caatggacta ctggggccag  720
ggtaccctgg ttacggtcag ctctggctcc gagctc                           756

SEQ ID NO: 2            moltype = AA  length = 252
FEATURE                 Location/Qualifiers
REGION                  1..252
                        note = Synthetic_Herceptin scFv amino acid sequence
source                  1..252
                        mol_type = protein
                        organism = synthetic construct
SEQUENCE: 2
KLDIQMTQSP SSLSASVGDR VTITCRASQD VNTAVAWYQQ KPGKAPKLLI YSASFLYSGV  60
PSRFSGSRSG TDFTLTISSL QPEDFATYYC QQHYTTPPTF GQGTKVEIKG ASGGGGSGGG  120
GSGGGGSSEV QLVESGGGLV QPGGSLRLSC AASGFNIKDT YIHWVRQAPG KGLEWVARIY  180
PTNGYTRYAD SVKGRFTISA DTSKNTAYLQ MNSLRAEDTA VYYCSRWGGD GFYAMDYWGQ  240
GTLVTVSSGS EL                                                     252

SEQ ID NO: 3            moltype = DNA  length = 219
FEATURE                 Location/Qualifiers
misc_feature            1..219
                        note = Synthetic_Wild-type Protein L B3 domain coding
                         nucleic acid sequence
source                  1..219
                        mol_type = other DNA
                        organism = synthetic construct
SEQUENCE: 3
atgccgaaag aagaggttac tattaaggct aatctgattt acgccgacgg aaaaacccag  60
accgctgagt tcaagggtac ttttgaagaa gcgacggcag aggcgtatcg gtacgcagat  120
ctgttagcga aagaaaatgg taagtatact gtagacgttg ccgacaaggg gtataccta  180
aatatcaagt tcgcaggtaa agagaaaacc ccggaagaa                        219

SEQ ID NO: 4            moltype = AA  length = 73
FEATURE                 Location/Qualifiers
REGION                  1..73
                        note = Synthetic_Wild-type Protein L B3 domain amino acid
                         sequence
source                  1..73
                        mol_type = protein
                        organism = synthetic construct
SEQUENCE: 4
MPKEEVTIKA NLIYADGKTQ TAEFKGTFEE ATAEAYRYAD LLAKENGKYT VDVADKGYTL  60
NIKFAGKEKT PEE                                                    73

SEQ ID NO: 5            moltype = DNA  length = 20
FEATURE                 Location/Qualifiers
misc_feature            1..20
                        note = Synthetic_EP-F error prone pcr forward primer
source                  1..20
                        mol_type = other DNA
                        organism = synthetic construct
SEQUENCE: 5
gcttgatatc gaattcctgc                                             20

SEQ ID NO: 6            moltype = DNA  length = 20
FEATURE                 Location/Qualifiers
misc_feature            1..20
                        note = Synthetic_T7 primer
source                  1..20
```

```
                        mol_type = other DNA
                        organism = synthetic construct
SEQUENCE: 6
taatacgact cactataggg                                                20

SEQ ID NO: 7            moltype = AA  length = 73
FEATURE                 Location/Qualifiers
REGION                  1..73
                        note = Synthetic_Protein L B3 domain variant EP1(E28A)
source                  1..73
                        mol_type = protein
                        organism = synthetic construct
SEQUENCE: 7
MPKEEVTIKA NLIYADGKTQ TAEFKGTFAE ATAEAYRYAD LLAKENGKYT VDVADKGYTL  60
NIKFAGKEKT PEE                                                       73

SEQ ID NO: 8            moltype = AA  length = 73
FEATURE                 Location/Qualifiers
REGION                  1..73
                        note = Synthetic_Protein L B3 domain variant EP2(E28G)
source                  1..73
                        mol_type = protein
                        organism = synthetic construct
SEQUENCE: 8
MPKEEVTIKA NLIYADGKTQ TAEFKGTFGE ATAEAYRYAD LLAKENGKYT VDVADKGYTL  60
NIKFAGKEKT PEE                                                       73

SEQ ID NO: 9            moltype = AA  length = 73
FEATURE                 Location/Qualifiers
REGION                  1..73
                        note = Synthetic_Protein L B3 domain variant BEP1(E28G/Y13F)
source                  1..73
                        mol_type = protein
                        organism = synthetic construct
SEQUENCE: 9
MPKEEVTIKA NLIFADGKTQ TAEFKGTFGE ATAEAYRYAD LLAKENGKYT VDVADKGYTL  60
NIKFAGKEKT PEE                                                       73

SEQ ID NO: 10           moltype = AA  length = 73
FEATURE                 Location/Qualifiers
REGION                  1..73
                        note = Synthetic_Protein L B3 domain variant (E28G/K43P)
source                  1..73
                        mol_type = protein
                        organism = synthetic construct
SEQUENCE: 10
MPKEEVTIKA NLIYADGKTQ TAEFKGTFGE ATAEAYRYAD LLAPENGKYT VDVADKGYTL  60
NIKFAGKEKT PEE                                                       73

SEQ ID NO: 11           moltype = AA  length = 73
FEATURE                 Location/Qualifiers
REGION                  1..73
                        note = Synthetic_Protein L B3 domain variant BEP3(E28G/D51V)
source                  1..73
                        mol_type = protein
                        organism = synthetic construct
SEQUENCE: 11
MPKEEVTIKA NLIYADGKTQ TAEFKGTFGE ATAEAYRYAD LLAKENGKYT VVVADKGYTL  60
NIKFAGKEKT PEE                                                       73

SEQ ID NO: 12           moltype = AA  length = 73
FEATURE                 Location/Qualifiers
REGION                  1..73
                        note = Synthetic_Protein L B3 domain variant BEP4(E28G/N60E)
source                  1..73
                        mol_type = protein
                        organism = synthetic construct
SEQUENCE: 12
MPKEEVTIKA NLIYADGKTQ TAEFKGTFGE ATAEAYRYAD LLAKENGKYT VDVADKGYTL  60
EIKFAGKEKT PEE                                                       73

SEQ ID NO: 13           moltype = DNA  length = 49
FEATURE                 Location/Qualifiers
misc_feature            1..49
                        note = Synthetic_28-F primer, wherein n is A, T, G, or C,
                         and k is G or T
source                  1..49
                        mol_type = other DNA
                        organism = synthetic construct
```

```
SEQUENCE: 13
gaccgctgag ttcaagggta cttttnnkga agcgacggca gaggcgtat              49

SEQ ID NO: 14          moltype = DNA  length = 49
FEATURE                Location/Qualifiers
misc_feature           1..49
                       note = Synthetic_28-R primer, wherein n is A, T, G, or C,
                        and m is A or C
source                 1..49
                       mol_type = other DNA
                       organism = synthetic construct
SEQUENCE: 14
atacgcctct gccgtcgctt cmnnaaaagt acccttgaac tcagcggtc              49

SEQ ID NO: 15          moltype = DNA  length = 45
FEATURE                Location/Qualifiers
misc_feature           1..45
                       note = Synthetic_13-F primer, wherein n is A, T, G, or C,
                        and k is G or T
source                 1..45
                       mol_type = other DNA
                       organism = synthetic construct
SEQUENCE: 15
ggttactatt aaggctaatc tgattnnkgc cgacggaaaa accca                  45

SEQ ID NO: 16          moltype = DNA  length = 45
FEATURE                Location/Qualifiers
misc_feature           1..45
                       note = Synthetic_13-R primer, wherein n is A, T, G, or C,
                        and m is A or C
source                 1..45
                       mol_type = other DNA
                       organism = synthetic construct
SEQUENCE: 16
tgggtttttc cgtcggcmnn aatcagatta gccttaatag taacc                  45

SEQ ID NO: 17          moltype = DNA  length = 46
FEATURE                Location/Qualifiers
misc_feature           1..46
                       note = Synthetic_43-F primer, wherein n is A, T, G, or C,
                        and k is G or T
source                 1..46
                       mol_type = other DNA
                       organism = synthetic construct
SEQUENCE: 17
gtacgcagat ctgttagcgn nkgaatatgg taagtatact gtagcg                 46

SEQ ID NO: 18          moltype = DNA  length = 47
FEATURE                Location/Qualifiers
misc_feature           1..47
                       note = Synthetic_43-R primer, wherein n is A, T, G, or C,
                        and m is A or C
source                 1..47
                       mol_type = other DNA
                       organism = synthetic construct
SEQUENCE: 18
cgtctacagt atacttacca tattcmnncg ctaacagatc tgcgtac                47

SEQ ID NO: 19          moltype = DNA  length = 47
FEATURE                Location/Qualifiers
misc_feature           1..47
                       note = Synthetic_51-F primer, wherein n is A, T, G, or C,
                        and k is G or T
source                 1..47
                       mol_type = other DNA
                       organism = synthetic construct
SEQUENCE: 19
gcgaaagaat atggtaagta tactgtannk gttgccgaca aggggta                47

SEQ ID NO: 20          moltype = DNA  length = 47
FEATURE                Location/Qualifiers
misc_feature           1..47
                       note = Synthetic_51-R primer, wherein n is A, T, G, or C,
                        and m is A or C
source                 1..47
                       mol_type = other DNA
                       organism = synthetic construct
SEQUENCE: 20
taccccttgt cggcaacmnn tacagtatac ttaccatatt ctttcgc                47
```

```
SEQ ID NO: 21          moltype = DNA  length = 44
FEATURE                Location/Qualifiers
misc_feature           1..44
                       note = Synthetic_60-F primer, wherein n is A, T, G, or C,
                        and k is G or T
source                 1..44
                       mol_type = other DNA
                       organism = synthetic construct
SEQUENCE: 21
ccgacaaggg gtataccttta nnkatcaagt tcgcaggtaa agag                   44

SEQ ID NO: 22          moltype = DNA  length = 44
FEATURE                Location/Qualifiers
misc_feature           1..44
                       note = Synthetic_60-R primer, wherein n is A, T, G, or C,
                        and m is A or C
source                 1..44
                       mol_type = other DNA
                       organism = synthetic construct
SEQUENCE: 22
ctctttacct gcgagcttga tmnntaaggt ataccccttg tcgg                    44

SEQ ID NO: 23          moltype = AA  length = 73
FEATURE                Location/Qualifiers
REGION                 1..73
                       note = Synthetic_Protein L B3 domain variant EPS1(E28L)
source                 1..73
                       mol_type = protein
                       organism = synthetic construct
SEQUENCE: 23
MPKEEVTIKA NLIYADGKTQ TAEFKGTFLE ATAEAYRYAD LLAKENGKYT VDVADKGYTL  60
NIKFAGKEKT PEE                                                     73

SEQ ID NO: 24          moltype = AA  length = 73
FEATURE                Location/Qualifiers
REGION                 1..73
                       note = Synthetic_Protein L B3 domain variant EPS2(E28P)
source                 1..73
                       mol_type = protein
                       organism = synthetic construct
SEQUENCE: 24
MPKEEVTIKA NLIYADGKTQ TAEFKGTFPE ATAEAYRYAD LLAKENGKYT VDVADKGYTL  60
NIKFAGKEKT PEE                                                     73

SEQ ID NO: 25          moltype = AA  length = 73
FEATURE                Location/Qualifiers
REGION                 1..73
                       note = Synthetic_Protein L B3 domain variant EPS3(E28W)
source                 1..73
                       mol_type = protein
                       organism = synthetic construct
SEQUENCE: 25
MPKEEVTIKA NLIYADGKTQ TAEFKGTFWE ATAEAYRYAD LLAKENGKYT VDVADKGYTL  60
NIKFAGKEKT PEE                                                     73

SEQ ID NO: 26          moltype = AA  length = 73
FEATURE                Location/Qualifiers
REGION                 1..73
                       note = Synthetic_Protein L B3 domain variant EPS4(E28G/K43E)
source                 1..73
                       mol_type = protein
                       organism = synthetic construct
SEQUENCE: 26
MPKEEVTIKA NLIYADGKTQ TAEFKGTFGE ATAEAYRYAD LLAEENGKYT VDVADKGYTL  60
NIKFAGKEKT PEE                                                     73

SEQ ID NO: 27          moltype = AA  length = 73
FEATURE                Location/Qualifiers
REGION                 1..73
                       note = Synthetic_Protein L B3 domain variant EPS5(E28G/D51T)
source                 1..73
                       mol_type = protein
                       organism = synthetic construct
SEQUENCE: 27
MPKEEVTIKA NLIYADGKTQ TAEFKGTFGE ATAEAYRYAD LLAKENGKYT VTVADKGYTL  60
NIKFAGKEKT PEE                                                     73

SEQ ID NO: 28          moltype = AA  length = 73
```

```
FEATURE                Location/Qualifiers
REGION                 1..73
                       note = Synthetic_Protein L B3 domain variant EPS6(E28G/N60F)
source                 1..73
                       mol_type = protein
                       organism = synthetic construct
SEQUENCE: 28
MPKEEVTIKA NLIYADGKTQ TAEFKGTFGE ATAEAYRYAD LLAKENGKYT VDVADKGYTL  60
FIKFAGKEKT PEE                                                    73

SEQ ID NO: 29          moltype = DNA  length = 48
FEATURE                Location/Qualifiers
misc_feature           1..48
                       note = Synthetic_SH13-F1 primer
source                 1..48
                       mol_type = other DNA
                       organism = synthetic construct
SEQUENCE: 29
ggttactatt aaggctaatc tgatttacgc cgacggaaaa acccagac              48

SEQ ID NO: 30          moltype = DNA  length = 48
FEATURE                Location/Qualifiers
misc_feature           1..48
                       note = Synthetic_SH13-F2 primer
source                 1..48
                       mol_type = other DNA
                       organism = synthetic construct
SEQUENCE: 30
ggttactatt aaggctaatc tgattgaggc cgacggaaaa acccagac              48

SEQ ID NO: 31          moltype = DNA  length = 48
FEATURE                Location/Qualifiers
misc_feature           1..48
                       note = Synthetic_SH13-R1 primer
source                 1..48
                       mol_type = other DNA
                       organism = synthetic construct
SEQUENCE: 31
gtctgggttt ttccgtcggc gtaaatcaga ttagccttaa tagtaacc              48

SEQ ID NO: 32          moltype = DNA  length = 48
FEATURE                Location/Qualifiers
misc_feature           1..48
                       note = Synthetic_SH13-R2 primer
source                 1..48
                       mol_type = other DNA
                       organism = synthetic construct
SEQUENCE: 32
gtctgggttt ttccgtcggc ctcaatcaga ttagccttaa tagtaacc              48

SEQ ID NO: 33          moltype = DNA  length = 47
FEATURE                Location/Qualifiers
misc_feature           1..47
                       note = Synthetic_SH43-F1 primer, wherein r is G or A
source                 1..47
                       mol_type = other DNA
                       organism = synthetic construct
SEQUENCE: 33
cgcagatctg ttagcgaaag aaraaggtaa gtatactgta gacgttg               47

SEQ ID NO: 34          moltype = DNA  length = 47
FEATURE                Location/Qualifiers
misc_feature           1..47
                       note = Synthetic_SH43-F2 primer
source                 1..47
                       mol_type = other DNA
                       organism = synthetic construct
SEQUENCE: 34
cgcagatctg ttagcgaaag aaccaggtaa gtatactgta gacgttg               47

SEQ ID NO: 35          moltype = DNA  length = 47
FEATURE                Location/Qualifiers
misc_feature           1..47
                       note = Synthetic_SH43-R1 primer, wherein y is C or T
source                 1..47
                       mol_type = other DNA
                       organism = synthetic construct
SEQUENCE: 35
caacgtctac agtatactta ccttyttctt tcgctaacag atctgcg               47
```

```
SEQ ID NO: 36          moltype = DNA  length = 47
FEATURE                Location/Qualifiers
misc_feature           1..47
                       note = Synthetic_SH43-R2 primer
source                 1..47
                       mol_type = other DNA
                       organism = synthetic construct
SEQUENCE: 36
caacgtctac agtatactta cctggttctt tcgctaacag atctgcg                47

SEQ ID NO: 37          moltype = DNA  length = 54
FEATURE                Location/Qualifiers
misc_feature           1..54
                       note = Synthetic_SH51-F1 primer, wherein w is A or T
source                 1..54
                       mol_type = other DNA
                       organism = synthetic construct
SEQUENCE: 37
gcgaaagaat atggtaagta tactgtagwc gttgccgaca aggggtatac ctta        54

SEQ ID NO: 38          moltype = DNA  length = 54
FEATURE                Location/Qualifiers
misc_feature           1..54
                       note = Synthetic_SH51-F2 primer
source                 1..54
                       mol_type = other DNA
                       organism = synthetic construct
SEQUENCE: 38
gcgaaagaat atggtaagta tactgtaacc gttgccgaca aggggtatac ctta        54

SEQ ID NO: 39          moltype = DNA  length = 54
FEATURE                Location/Qualifiers
misc_feature           1..54
                       note = Synthetic_SH51-R1 primer, wherein w is A or T
source                 1..54
                       mol_type = other DNA
                       organism = synthetic construct
SEQUENCE: 39
taaggtatac cccttgtcgg caacgwctac agtatactta ccatattctt tcgc        54

SEQ ID NO: 40          moltype = DNA  length = 47
FEATURE                Location/Qualifiers
misc_feature           1..47
                       note = Synthetic_SH51-R2 primer
source                 1..47
                       mol_type = other DNA
                       organism = synthetic construct
SEQUENCE: 40
caacgtctac agtatactta cctggttctt tcgctaacag atctgcg                47

SEQ ID NO: 41          moltype = DNA  length = 45
FEATURE                Location/Qualifiers
misc_feature           1..45
                       note = Synthetic_SH60-F1 primer
source                 1..45
                       mol_type = other DNA
                       organism = synthetic construct
SEQUENCE: 41
gccgacaagg ggtatacctt aaatatcaag ttcgcaggta aagag                  45

SEQ ID NO: 42          moltype = DNA  length = 45
FEATURE                Location/Qualifiers
misc_feature           1..45
                       note = Synthetic_SH60-F2 primer
source                 1..45
                       mol_type = other DNA
                       organism = synthetic construct
SEQUENCE: 42
gccgacaagg ggtatacctt agagatcaag ttcgcaggta aagag                  45

SEQ ID NO: 43          moltype = DNA  length = 45
FEATURE                Location/Qualifiers
misc_feature           1..45
                       note = Synthetic_SH60-F3 primer
source                 1..45
                       mol_type = other DNA
                       organism = synthetic construct
SEQUENCE: 43
```

```
gccgacaagg ggtatacctt atttatcaag ttcgcaggta aagag                45

SEQ ID NO: 44          moltype = DNA  length = 45
FEATURE                Location/Qualifiers
misc_feature           1..45
                       note = Synthetic_SH60-R1 primer
source                 1..45
                       mol_type = other DNA
                       organism = synthetic construct
SEQUENCE: 44
ctctttacct gcgaacttga tatttaaggt ataccccttg tcggc                45

SEQ ID NO: 45          moltype = DNA  length = 45
FEATURE                Location/Qualifiers
misc_feature           1..45
                       note = Synthetic_SH60-R2 primer
source                 1..45
                       mol_type = other DNA
                       organism = synthetic construct
SEQUENCE: 45
ctctttacct gcgaacttga tctctaaggt ataccccttg tcggc                45

SEQ ID NO: 46          moltype = DNA  length = 45
FEATURE                Location/Qualifiers
misc_feature           1..45
                       note = Synthetic_SH60-R3 primer
source                 1..45
                       mol_type = other DNA
                       organism = synthetic construct
SEQUENCE: 46
ctctttacct gcgaacttga taaataaggt ataccccttg tcggc                45

SEQ ID NO: 47          moltype = AA  length = 73
FEATURE                Location/Qualifiers
REGION                 1..73
                       note = Synthetic_Protein L B3 domain variant mBF
                        (Y13F/E28G/K43P)
source                 1..73
                       mol_type = protein
                       organism = synthetic construct
SEQUENCE: 47
MPKEEVTIKA NLIFADGKTQ TAEFKGTFGE ATAEAYRYAD LLAPENGKYT VDVADKGYTL  60
NIKFAGKEKT PEE                                                   73

SEQ ID NO: 48          moltype = DNA  length = 876
FEATURE                Location/Qualifiers
misc_feature           1..876
                       note = Synthetic_Protein L B3 domain variant mBF repeat
                        (4mBF) coding nucleic acid sequence
source                 1..876
                       mol_type = other DNA
                       organism = synthetic construct
SEQUENCE: 48
atgccgaaag aagaggttac tattaaggct aatctgattt tcgccgacgg aaaaacccag  60
accgctgagt tcaagggtac ttttggggaa gcgacggcag aggcgtatcg gtacgcagat  120
ctgttagcgc cagaaaatgg taagtatact gtagacgttg ccgacaaggg gtataccta  180
aatatcaagt tcgcaggtaa agagaaaacc ccggaagaaa tgccgaaaga agaggttact  240
attaaggcta atctgatttt cgccgacgga aaaacccaga ccgctgagtt caagggtact  300
tttggggaag cgacggcaga ggcgtatcgg tacgcagatc tgttagcgcc agaaaatggt  360
aagtatactg tagacgttgc cgacaagggg tataccttaa atatcaagtt cgcaggtaaa  420
gagaaaaccc cggaagaaat gccgaaagaa gaggttacta ttaaggctaa tctgattttc  480
gccgacggaa aaacccagac cgctgagttc aagggtactt ttggggaagc gacggcagag  540
gcgtatcggt acgcagatct gttagcgcca gaaaatggta agtatactgt agacgttgcc  600
gacaaggggt ataccttaaa tatcaagttc gcaggtaaag agaaaacccc ggaagaaatg  660
ccgaaagaag aggttactat taaggctaat ctgattttcg ccgacggaaa aacccagacc  720
gctgagttca agggtacttt tggggaagcg acggcagagg cgtatcggta cgcagatctg  780
ttagcgccag aaaatggtaa gtatactgta gacgttgccg acaaggggta taccttaaat  840
atcaagttcg caggtaaaga gaaaaccccg gaagaa                          876

SEQ ID NO: 49          moltype = AA  length = 292
FEATURE                Location/Qualifiers
REGION                 1..292
                       note = Synthetic_Protein L B3 domain variant mBF repeat
                        (4mBF)
source                 1..292
                       mol_type = protein
                       organism = synthetic construct
SEQUENCE: 49
MPKEEVTIKA NLIFADGKTQ TAEFKGTFGE ATAEAYRYAD LLAPENGKYT VDVADKGYTL  60
```

-continued

```
NIKFAGKEKT PEEMPKEEVT IKANLIFADG KTQTAEFKGT FGEATAEAYR YADLLAPENG  120
KYTVDVADKG YTLNIKFAGK EKTPEEMPKE EVTIKANLIF ADGKTQTAEF KGTFGEATAE  180
AYRYADLLAP ENGKYTVDVA DKGYTLNIKF AGKEKTPEEM PKEEVTIKAN LIFADGKTQT  240
AEFKGTFGEA TAEAYRYADL LAPENGKYTV DVADKGYTLN IKFAGKEKTP EE          292

SEQ ID NO: 50          moltype = AA  length = 719
FEATURE                Location/Qualifiers
REGION                 1..719
                       note = Synthetic_Protein L (AAA25612.1), wherein 1..18
                        region is a signal peptide
source                 1..719
                       mol_type = protein
                       organism = synthetic construct
SEQUENCE: 50
MAALAGAIVV TGGVGSYAAD EPIDLEKLEE KRDKENVGNL PKFDNEVKDG SENPMAKYPD  60
FDDEASTRFE TENNEFEEKK VVSDNFFDQS EHPFVENKEE TPETPETDSE EEVTIKANLI  120
FANGSTQTAE FKGTFEKATS EAYAYADTLK KDNGEYTVDV ADKGYTLNIK FAGKEKTPEE  180
PKEEVTIKAN LIYADGKTQT AEFKGTFEEA TAEAYRYADA LKKDNGEYTV DVADKGYTLN  240
IKFAGKEKTP EEPKEEVTIK ANLIYADGKT QTAEFKGTFE EATAEAYRYA DLLAKENGKY  300
TVDVADKGYT LNIKFAGKEK TPEEPKEEVT IKANLIYADG KTQTAEFKGT FAEATAEAYR  360
YADLLAKENG KYTADLEDGG YTINIRFAGK KVDEKPEEKE QVTIKENIYF EDGTVQTATF  420
KGTFAEATAE AYRYADLLSK EHGKYTADLE DGGYTINIRF AGKEEPEETP EKPEVQDGYA  480
SYEEAEAAAK EALKNDDVNK SYTIRQGADG RYYYVLSPVE AEEEKPEAQN GYATYEEAEA  540
AAKKALENDP INKSYSIRQG ADGRYYYVLS PVEAETPEKP VEPSEPSTPD VPSNPSNPST  600
PDVPSTPDVP SNPSTPEVPS NPSTPGNEEK PGNEQKPGNE QKPGNEQKPG NEQKPGNEQK  660
PDQPSKPEKE ENGKGGVDSP KKKEKAALPK AGSEAEILTL AAASLSSVAG AFISLKKRK   719
```